(12) United States Patent
Zhang et al.

(10) Patent No.: US 8,440,409 B2
(45) Date of Patent: May 14, 2013

(54) PROTEIN C INHIBITOR AS A BIOMARKER FOR PROSTATE CANCER

(75) Inventors: Zhen Zhang, Dayton, MD (US); Daniel W. Chan, Clarksville, MD (US); Carolyn N. Rosenzweig, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 744 days.

(21) Appl. No.: 11/992,000

(22) PCT Filed: Sep. 19, 2006

(86) PCT No.: PCT/US2006/036538
§ 371 (c)(1),
(2), (4) Date: May 12, 2009

(87) PCT Pub. No.: WO2007/035766
PCT Pub. Date: Mar. 29, 2007

(65) Prior Publication Data
US 2009/0221672 A1    Sep. 3, 2009

Related U.S. Application Data

(60) Provisional application No. 60/718,843, filed on Sep. 19, 2005.

(51) Int. Cl.
*G01N 33/53*    (2006.01)
*G01N 33/574*    (2006.01)

(52) U.S. Cl.
USPC .......................................... 435/7.1; 435/7.23

(58) Field of Classification Search .................. None
See application file for complete search history.

(56) References Cited

U.S. PATENT DOCUMENTS

| 6,399,078 | B1 | 6/2002 | Devico et al. |
| 6,692,643 | B2 | 2/2004 | Sulkowski et al. |
| 6,936,424 | B1 | 8/2005 | Watkins et al. |
| 2009/0208921 | A1* | 8/2009 | Tempst et al. ............... 435/4 |

FOREIGN PATENT DOCUMENTS

| JP | 08-075737 | * | 3/1996 |
| WO | WO-00/47626 | | 8/2000 |

OTHER PUBLICATIONS

Cao et al (The Prostate, 2003, 57:196-204) in IDS.*
Grizzle et al (Disease markers, 2003-2004, 19:185-195).*
Tockman et al (Cancer Res., 1992, 52:2711s-2718s).*
Cao et al (The Prostate, 2003, 57:196-204).*
Rosenzweig et al (Journal of Urology, 2009, 181:1407-1414).*
Machine English translation of JP 08-075737, Suzuki et al, published Mar. 1996.*
White et al (Proc Amer Assoc Cancer Res, Apr. 2005, 46, abstract #4794).*
Glasscock L N et al: "Protein C inhibitor (plasminogen activator inhibitor-3) expression in the CWR22 prostate cancer xenograft" Esperimental and Molecular Pathology, Academic Press, US, vol. 79. No. 1, Aug. 1, 2005, pp. 23-32.
Cao You et al: "Expression of protein C inhibitor (PCI) in benign and malignant prostatic issues." Prostate, vol. 57, No. 3, Oct. 6, 2003, pp. 196-204.

* cited by examiner

*Primary Examiner* — Laura B Goddard
(74) *Attorney, Agent, or Firm* — Edwards Wildman Palmer LLP; Peter F. Corless; Richard B. Emmons

(57) ABSTRACT

The present invention provides a protein-based biomarker, Protein C Inhibitor (PCI) that is useful in qualifying prostate cancer status in a patient. In particular, the biomarker of this invention is useful to classify a subject sample as prostate cancer or non-prostate cancer. The biomarker can be detected by SELDI mass spectrometry.

5 Claims, 25 Drawing Sheets

FIG. 10

ProteinProspector search input.

Database SwissProt2005.01.06 ▼ DNA Frame translation 3 ▼ | Digest No enzyme ▼
Search Hits ☐ From msfit ▼ Filename lastres1 ▼ | Max.# of missed cleavages 1
Species ▼ | Cys modified by: acrylamide ▼
Protein MW (from 1000 to 100000 Da) All ☑
Start Search
Parent tolerance 150 ▼ ppm ▼ | max. % Unmatched Ions ▼ 30
Fragment tolerance 100 | Maximun Reported Hits 25
Display Graphs ☐ | Allowed Fragment Ion types(specific to instrument type selected)
Fragment Ion Tag | Instrument MALDI-TOF ▼
Masses are monoisotopic ▼ | AA Composition(based on immonium and related ions)
Mass (m, z) Charge (z) | is calculated automatically
 | Sample ID (comment):

3889.70
358.22
559.39
1253.84
1270.83
1272.83
1289.78
1367.89
1384.9
2348.40
2372.52

| FIG. 11A |
|----------|
| FIG. 11B |
| FIG. 11C |

FIG. 11

Database search result

Parameters

Database Started SwissProt2005.01.06
Digest Used : No enzyme
Max. # Missed Cleavages 1
Peptide N terminus: Hydrogen
Peptide C terminus : Free Acid
Cysteine Modification : acrylamide
Instrument Name : MALDI-TOF
Max. % unmatched Ions 30
Ion Types Considered a-NH3, a, b, b-NH3, b-H2O, y, y-NH3 y-H2O, l, i, m, P, S
Search Mode : identity
Peptide Masses are monoisotopic Pre Search Results Number of entries in the database : 161074
Full Molecular Weight range : 161074 entries
Full pI range : 161074 entries
Pre searches select : 161074 entries Data Set I Results Number or sequences passing through parent mass filter : 555317
MS Tag search selects 1 entry Parent mass : 3889.7000(+/-0.58 Da)
15 Ions used in search 358.22, 559.39, 1253.84, 1270.83, 1289.78, 1367.89, 1384.90, 2348.40, 2372.52, 2390.44, 2446.18, 2471.47 2487.52, 2505.52(+/- 100.00 ppm)
Max.#Unmatched = 4

FIG. 11A

Result Summary

| Rank | # unmatched ions | Measured Sequence | MH+ Calculated (Da) | MH+ Error (ppm) | MS Digest Index # | Protein MW (Da)/pI | Ascension # | Species | Protein Name |
|---|---|---|---|---|---|---|---|---|---|
| 1 | 4 | (R)SARLNSQRLVFN RPFLMFIVDNNDFL GKVNRF(-) | 18889.1539 | 140 | 122.634 | 457829.3 | P05154 | HUMAN | Plasma serine protease inhibitor precursor(PCI) (Protein C inhibitor) (Plasmotogen activator inhibitor-3) (PAI3) (Acrosonial serve protease inhibitor) |

Detailed Results

| Rank | # Unmatched Ions | Measured Sequence | MH+ Calculated (Da) | MH+ Error (ppm) | MS Digest Index # | Protein MW (Da)/pI | Ascension # | Species | Protein Names |
|---|---|---|---|---|---|---|---|---|---|
| 1 | 4 | (R)SARLNSQRLVFN RPFLMFIVDNNDFL GKVNRF(-) | 1889.1539 | 140 | 122.634 | 457829.3 | P05154 | HUMAN | Plasma serine protease inhibitor precursor(PCI) (Protein C inhibitor) (Plasmotogen activator inhibitor-3) (PAI3) (Acrosonial serve protease inhibitor) |

FIG. 11B

| Fragment Ion (m/z) | 350.22 | 559.39 | 1253.84 | 1270.03 | 1272.83 | 1289.78 | 1367.89 | 1384.90 | 2348.40 | 2372.52 |
|---|---|---|---|---|---|---|---|---|---|---|
| Ion Type Delta ppm | PFL 19 | LFLGK 52 | $y_{11}$ $NH_3$ 82 | $y_{11}$ 52 | $b_{11}$ 88 | RLNSQRLVFNR-$NH_3$ 91 $y_{12}NH_3$ 80 | RLNSQRLVFNR 78 $y_{12}$ 68 | DNNILFLGKVNR 94 RLNSQRLVENR 78 | | $b_{20}$ $H_2O$ 85 |

| 2390.44 | 2446.48 |
|---|---|
| SQRLVFNRPFLMFTVDNNIL 28 51 $b_{20}$ 47 ARLNSQRLVFNRPFLMFIVD 28 47 | RLVFNRPFLMFIIVDNNILFL RLVFNRPFLMFIIVDNNILFL $NH_3$ 54 |

| Fragment Ion (m/z) | 2471.47 | 2487.52 | 2505.52 |
|---|---|---|---|
| Ion Type Delta ppm | | $b_{21}$-$H_2O$ 70 | $b_{21}$ 66 |

FIG. 11C

Swiss-Prot: IPSP_HUMAN

The section of the sequence IPSP_HUMAN (P05154) you have selected corresponds to:

SITE    373    374    Reactive bond.

In one-letter code:

```
       1           11          21          31          41          51
  1  MQLFLLCLV   LLSPQGASLH  RHHPREMKKR  VEDLHVGATV  APSSRRDFTF  DLYRAKASAA    60
 61  PSQNIFFSPV  SISMSLAMLS  LGAGSSTKMQ  ILEGLGLNLQ  KSSEKELHRG  FQQLLQELNQ   120
121  PRDGFQLSLG  NALFTDLVVD  LQDTFVSAMK  TLYLADTFPT  NFRDSAGAMK  QINDYVAKQT   180
181  KGKIVDLLKN  LDSNAVVTMV  NYIFFKAKWE  TSFNHKGTQE  QDFYVTSETV  VRVPMMSRED   240
241  QYHYLLDRNL  SCRVVGVPYQ  GNATALFILP  SEGKMQQVEN  GLSEKTLRKW  LKMFKKRQLE   300
301  LYLPKFSIEG  SYQLEKVLPS  LGISNVFTSH  ADLSGISNHS  NIQVSEMVHK  AVVEVDESGT   360
361  RAAAATGTIF  TFRSARLNSQ  RLVENRPFLM  FIVDNNILFL  GKVNRP
```

FIG. 13

Theoretical MW of the C-terminal fragment of Protein C Inhibitor

Theoretical pI/Mw for the protein sequence
SARLNSQRLV ... ILFLGKVNRP:

Theoretical pI/Mw: 12.00 / 3890.61

FIG. 14

ROC analysis of PCI peak separating PCa patients with Gleason score at 5-7 from PCa patients with Gleason score at 8 and above.

ROC analysis of PCI peak in separating PCa patients from patients with benign prostate disease

PROTEIN C INHIBITOR AS A BIOMARKER FOR PROSTATE CANCER

RELATED APPLICATIONS

This application claims the benefit of U.S. Provisional Application No. 60/718,843, filed Sep. 19, 2005, the entire contents of which are expressly incorporated herein by reference.

SEQUENCE LISTING

The instant application contains a Sequence Listing which has been submitted in ASCII format via EFS-Web and is hereby incorporated by reference in its entirety. Said ASCII copy, created on Sep. 30, 2011, is named 64161716.txt and is 6,815 bytes in size.

FIELD OF THE INVENTION

The invention provides for a biomarker important in the detection of prostate cancer. The marker was identified by distinguishing the serum protein profile in prostate cancer patients from healthy individuals using SELDI analysis. The present invention relates the biomarker to a system and method in which the biomarker is used for the qualification of prostate cancer status. The present invention also identifies the biomarker as the known protein, Protein C Inhibitor (PCI).

BACKGROUND OF THE INVENTION

Prostate carcinoma is the most common type of cancer in men. In the year 2002, it is expected to account for 189,000 new cancer cases among men and 30,200 will die from this disease. Early detection of prostate cancer when the cancer is confined to the prostate gland has the best chance of cure through radical prostatectomy (surgery). Although PSA is considered as an effective tumor marker and is for all intents and purposes organ specific, it is not cancer specific. There is considerable overlap in PSA concentrations in men with prostate cancer and men with benign prostatic diseases. PSA could not differentiate men with organ confined prostate cancer (who would benefit from surgery) from those men with non-organ confined prostate cancer (who would not benefit from surgery). Therefore, PSA is not effective in selecting patients for radical prostatectomy.

Early detection and diagnosis of prostate cancer currently relies on digital rectal examinations (DRE), prostate specific antigen (PSA) measurements, transrectal ultrasonography (TRUS), and transrectal needle-biopsy (TRNB). At present, serum PSA measurement in combination with DRE represents the leading tool used to detect and diagnose prostate cancer.

Commercially-available PSA assays are commonly sold as kits, and the assays performed in regional or local laboratories. However, prostate specific antigen (PSA) and prostatic acid phosphatase (PAP), have limited therapeutic and diagnostic potential. For example, PSA levels do not always correlate well with the presence of prostate cancer, being positive in a percentage of non-prostate cancer cases, including benign prostatic hyperplasia (BPH). Furthermore, PSA measurements correlate with prostate volume, and do not indicate the level of metastasis.

These kits play a part in the current strategy for early detection of prostate cancer. A problem arises, however, when a modestly abnormal PSA value (4-10 ng/ml) is encountered in the context of a negative digital rectal exam (DRE). Only 20-30% of individuals with such findings will demonstrate carcinoma on biopsy (Kantoff and Talcott, 8(3) *Hematol. Oncol. Clinics N Amer* 555 (1994)). It has therefore been important to develop strategies that increase the positive predictive value of PSA testing. Such strategies now include establishing age-adjusted normal ranges, determining the free to total PSA ratio, correcting for prostate gland mass (density), and calculating the rate of change of PSA values (Kantoff and Talcott, 8(3) *Hematol. Oncol Clinics N Amer* 555 (1994) and Brawer, 45 CA-A *Cancer J Clinicians* 148 (1995)). While each of these strategies has made a contribution, considerable uncertainty nevertheless remains about how to proceed with a patient who is PSA positive and DRE negative.

In addition, PSA is not a disease-specific marker, as elevated levels of PSA are detectable in a large percentage of patients with BPH and prostatitis (25-86%) (Gao et al., 1997, *Prostate* 31: 264-281), as well as in other nonmalignant disorders and in some normal men, a factor which significantly limits the diagnostic specificity of this marker. For example, elevations in serum PSA of between 4 to 10 ng/ml are observed in BPH, and even higher values are observed in prostatitis, particularly acute prostatitis. BPH is an extremely common condition in men. Further confusing the situation is the fact that serum PSA elevations may be observed without any indication of disease from DRE, and vice-versa. Moreover, it is now recognized that PSA is not prostate-specific (Gao et al., supra, for review).

There is also a need for more reliable and informative staging and prognostic methods in the management of advanced prostate cancer. Clinically staging prostate tumors relies on rectal examination to determine whether the tumor remains within the borders of the prostatic capsule (locally confined) or extends beyond it (locally advanced), in combination with serum PSA determinations and transrectal ultrasound guided biopsies. However, none of these techniques has proven reliable for predicting progression of the disease.

A need therefore, exists which can specifically identify prostate cancer, can distinguish prostate cancer from benign hyperplasia, can identify prostate cancer even though PSA levels are low, and identify the stages of disease progression.

SUMMARY OF THE INVENTION

The present invention provides sensitive and quick methods and kits that are useful for determining the prostate cancer status by measuring a specific biomarker. The measurement of this marker in patient samples provides information that diagnosticians can correlate with a probable diagnosis of human cancer or a negative diagnosis (e.g., normal or disease-free). The marker is characterized by molecular weight and its known protein identity, Protein C Inhibitor ("PCI"). The marker can be resolved from other proteins in a sample by using a variety of fractionation techniques, e.g., chromatographic separation coupled with mass spectrometry, protein capture using immobilized antibodies or by traditional immunoassays. In preferred embodiments, the method of resolution involves Surface-Enhanced Laser Desorption/Ionization ("SELDI") mass spectrometry, in which the surface of the mass spectrometry probe comprises adsorbents that bind the markers.

The present invention provides a method of qualifying prostate cancer status in a subject comprising (a) measuring the PCI biomarker in a sample from the subject, and (b) correlating the measurement with prostate cancer status, in particular with a Gleason Score. In certain methods, the measuring step comprises detecting the presence or absence of the marker in the sample. In other methods, the measuring step comprises quantifying the amount of marker in the sample. In other methods, the measuring step comprises qualifying the type of biomarker in the sample.

In certain embodiments, the present invention can determine the distinction between patients with prostate cancer from those with benign prostate disease among men with an elevated level of serum PSA. The majority of such patients have a serum free to total PSA ratio in the range of 10-20% (or equivalent range by complex to total PSA ratio), a diagnostic gray zone. The disclosed biomarker has the potential to improve the detection of cancer in this range.

The invention also relates to methods wherein the measuring step comprises: providing a subject sample of blood or urine or a blood/urine derivative; fractionating proteins in the sample on an anion exchange resin and collecting fractions that contain PCI from the fractions on a surface of a substrate comprising capture reagents that bind this protein biomarkers. The blood derivative is, e.g., serum or plasma. In preferred embodiments, the substrate is a SELDI probe comprising an IMAC copper surface and wherein the protein biomarkers are detected by SELDI. In other embodiments, the substrate is a SELDI probe comprising biospecific affinity reagents that bind PCI and wherein the protein biomarker is detected by SELDI. In other embodiments, the substrate is a microtiter plate comprising biospecific affinity reagents that bind PCI and the protein biomarker is detected by immunoassay.

In certain embodiments, the methods further comprise managing subject treatment based on the status determined by the method. For example, if the result of the methods of the present invention is inconclusive or there is reason that confirmation of status is necessary, the physician may order more tests. Alternatively, if the status indicates that surgery is appropriate, the physician may schedule the patient for surgery. Likewise, if the result of the test is positive, e.g., the status is late stage prostate cancer or if the status is otherwise acute, no further action may be warranted. Furthermore, if the results show that treatment has been successful, no further management may be necessary.

The invention also provides for such methods where the PCI biomarker is measured again after subject management. In these instances, the step of managing subject treatment is then repeated and/or altered depending on the result obtained. In preferred embodiment, PCI is measured after treatment, alone or in combination with C4a, to determine the possibility of recurrence.

The term "prostate cancer status" refers to the status of the disease in the patient. Examples of types of prostate cancer statuses include, but are not limited to, the subject's risk of cancer, the presence or absence of disease, the stage of disease in a patient, and the effectiveness of treatment of disease. Other statuses and degrees of each status are known in the art.

In certain preferred embodiments, the method further comprises measuring at least one previously known marker (herein referred to as "Marker X") in a sample from the subject and correlating measurement of the at least one Marker X and the measurement of PCI with prostate cancer status. In certain embodiments only one Marker X is measured, in addition to the PCI marker, while in other embodiments more than one Marker X is measured.

Examples of Marker X include known prostate cancer biomarkers including but not limited to, C4a, APOC1, BRCA1, CHGA, CHGB, CLU, COL1A1, COL6A1, EGF, ERBB2, ERK8, FGF1, FGF10, FGF11, FGF13, FGF14, FGF16, FGF17, FGF18, FGF2, FGF20, FGF21, FGF22, FGF23, FGF3, FGF4, FGF5, FGF6, FGF7, FGF8, FGF9, GNRH1, IGF1, IGF2, IGFBP3, IGFBP6, IL12A, IL1A, IL1B, IL2, IL24, NHA, INSL3, INSL4, KLK10, KLK12, KLK13, KLK14, KLK15, KLK3, KLK4, KLK5, KLK6, KLK9, MMP2, MMP9, MSMB, NTN4, ODZ1, PAP, PLAU, PRL, PSAP, SERPINA3, SHBG, TGFA, TIMP3, VEGF and protein variants (e.g., cleavage forms, isoforms) of the markers.

The PCI marker of the invention can be characterized in one or more of several respects. In particular, in one aspect, this marker is characterized by molecular weight under the conditions specified herein, particularly as determined by mass spectral analysis. In another aspect, the marker can be characterized by features of the marker's mass spectral signature such as size (including area) and/or shape of the marker's spectral peaks, features including proximity, size and shape of neighboring peaks, etc. In yet another aspect, the marker can be characterized by affinity binding characteristics, particularly ability to binding to an IMAC copper adsorbent under specified conditions, however, other metals, e.g., nickel, may also be used. In preferred embodiments, marker of the invention may be characterized by each of such aspects, i.e. molecular weight, mass spectral signature and IMAC-Cu absorbent binding.

For the mass values of the marker disclosed herein, the mass accuracy of the spectral instrument is considered to be about within +/−0.15 percent of the disclosed molecular weight value. Additionally, to such recognized accuracy variations of the instrument, the spectral mass determination can vary within resolution limits of from about 400 to 1000 m/dm, where m is mass and dm is the mass spectral peak width at 0.5 peak height. Those mass accuracy and resolution variances associated with the mass spectral instrument and operation thereof are reflected in the use of the term "about" in the disclosure of the mass of the marker. It is also intended that such mass accuracy and resolution variances and thus meaning of the term "about" with respect to the markers disclosed herein is inclusive of variants of the marker as may exist due to sex, genotype and/or ethnicity of the subject and the particular cancer or origin or stage thereof.

The present invention further provides a method of qualifying prostate cancer status in a subject comprising (a) measuring the PCI biomarker in a sample from the subject, and (b) correlating the measurement with prostate cancer status. In certain methods, the measuring step comprises detecting the presence or absence of the marker in the sample. In other methods, the measuring step comprises quantifying the amount of marker in the sample.

The accuracy of a diagnostic test is characterized by a Receiver Operating Characteristic curve ("ROC curve"). An ROC is a plot of the true positive rate against the false positive rate for the different possible cutpoints of a diagnostic test. An ROC curve shows the relationship between sensitivity and specificity. That is, an increase in sensitivity will be accompanied by a decrease in specificity. The closer the curve follows the left axis and then the top edge of the ROC space, the more accurate the test. Conversely, the closer the curve comes to the 45-degree diagonal of the ROC graph, the less accurate the test. The area under the ROC is a measure of test accuracy. The accuracy of the test depends on how well the test separates the group being tested into those with and without the disease in question. An area under the curve (referred to as "AUC") of 1 represents a perfect test, while an area of 0.5 represents a less useful test. Thus, biomarker and diagnostic methods of the present invention have an AUC greater than 0.50, more preferred tests have an AUC greater than 0.60, more preferred tests have an AUC greater than 0.70.

Preferred methods of measuring the PCI biomarker include use of a biochip array. Biochip arrays useful in the invention include protein and nucleic acid arrays. One or more markers are captured on the biochip array and subjected to laser ionization to detect the molecular weight of the marker. Analysis of the marker is, for example, by molecular weight of the marker against a threshold intensity that is normalized against total ion current. Preferably, logarithmic transformation is used for reducing peak intensity ranges to limit the number of markers detected.

In preferred methods of the present invention, the step of correlating the measurement of the PCI biomarker with prostate cancer status is performed by a software classification algorithm. Preferably, data is generated on immobilized subject samples on a biochip array, by subjecting said biochip array to laser ionization and detecting intensity of signal for mass/charge ratio; and, transforming the data into computer readable form; and executing an algorithm that classifies the data according to user input parameters, for detecting signals that represent marker present in prostate cancer patients and are lacking in non-cancer subject controls.

Preferably the biochip surfaces are, for example, ionic, anionic, comprised of immobilized nickel ions, comprised of a mixture of positive and negative ions, comprised of one or more antibodies, single or double stranded nucleic acids, proteins, peptides or fragments thereof, amino acid probes, or phage display libraries.

In other preferred methods one or more of the marker is measured using laser desorption/ionization mass spectrometry, comprising providing a probe adapted for use with a mass spectrometer comprising an adsorbent attached thereto, and contacting the subject sample with the adsorbent, and; desorbing and ionizing the marker from the probe and detecting the deionized/ionized markers with the mass spectrometer.

Preferably, the laser desorption/ionization mass spectrometry comprises: providing a substrate comprising an adsorbent attached thereto; contacting the subject sample with the adsorbent; placing the substrate on a probe adapted for use with a mass spectrometer comprising an adsorbent attached thereto; and, desorbing and ionizing the marker from the probe and detecting the desorbed/ionized marker with the mass spectrometer.

The adsorbent can for example be hydrophobic, hydrophilic, ionic or metal chelate adsorbent, such as, nickel or an antibody, single- or double stranded oligonucleotide, amino acid, protein, peptide or fragments thereof.

The methods of the present invention can be performed on any type of patient sample that would be amenable to such methods, e.g., blood, serum and plasma.

The present invention also provides kits comprising (a) a capture reagent that binds the PCI biomarker, and (b) a container comprising the biomarker. In preferred embodiments, the capture reagent binds the biomarker. While the capture reagent can be any type of reagent, preferably the reagent is a SELDI probe. The capture reagent may also bind other known biomarkers, e.g., Marker X. In certain preferred embodiments, the kit of further comprises a second capture reagent that binds the biomarker that the first capture reagent did not bind.

In certain kits of the present invention, the capture reagent comprises an immobilized metal chelate ("IMAC").

Certain kits of the present invention further comprise a wash solution that selectively allows retention of the bound biomarker to the capture reagent as compared with other biomarkers after washing.

The invention also provides kits comprising (a) a first capture reagent that binds the PCI biomarker, and (b) instructions for using the capture reagent to measure the biomarker. In certain of these kits, the capture reagent comprises an antibody. Furthermore, some kits further comprise an MS probe to which the capture reagent is attached or is attachable. In some kits, the capture reagent comprises an IMAC. The kits may also contain a wash solution that selectively allows retention of the bound biomarker to the capture reagent as compared with other biomarkers after washing. Preferably, the kit comprises written instructions for use of the kit for determining prostate cancer status and the instructions provide for contacting a test sample with the capture reagent and measuring one or more biomarkers retained by the capture reagent.

The kit also provides for a capture reagent, which is an antibody, single or double stranded oligonucleotide, amino acid, protein, peptide or fragments thereof.

Measurement of the protein biomarker using the kit, is by mass spectrometry or immunoassays such as an ELISA.

Purified proteins for detection of prostate cancer and/or generation of antibodies for further diagnostic assays are also provided for. Purified proteins include a purified peptide of PCI. The invention also provides this purified peptide further comprising a detectable label.

In another embodiment, non-invasive medical imaging techniques such as transvaginal ultrasound, positron emission tomography (PET) or single photon emission computerized tomography (SPECT) imaging are particularly useful for the detection of cancer, coronary artery disease and brain disease. Ultrasound with Doppler flow, PET, and SPECT imaging show the chemical functioning of organs and tissues, while other imaging techniques—such as X-ray, CT and MRI—primarily show structure. The use of ultrasound with flow, PET and SPECT imaging has become increasingly useful for qualifying and monitoring the development of diseases such as prostate cancer.

The PCI peptide biomarker disclosed herein, or fragments thereof, can be used in the context of PET and SPECT imaging applications. After modification with appropriate tracer residues for PET or SPECT applications, the PCI biomarker that interacts with tumor proteins can be used to image the deposition of biomarkers in prostate cancer patients.

Other aspects of the invention are descried infra.

BRIEF DESCRIPTION OF THE DRAWINGS

FIG. 10 is a representative example of protein prospector search input.

FIG. 11 is a representative example a database search result. FIG. 11B discloses SEQ ID NO: 1 as the measured sequence. FIG. 11C discloses SEQ ID NOS 2-8, respectively in order of appearance.

FIG. 12 discloses SEQ ID NO: 9.

FIG. 13 is an illustration of the amino acid sequence of PCI (SEQ ID NO: 10).

FIG. 14 is an illustration of the theoretical molecular weight of PCI. FIG. 14 discloses residues 1-10 and 24-33 of SEQ ID NO: 9, respectively in order of appearance.

DETAILED DESCRIPTION OF THE INVENTION

1. Introduction

Figure 1:
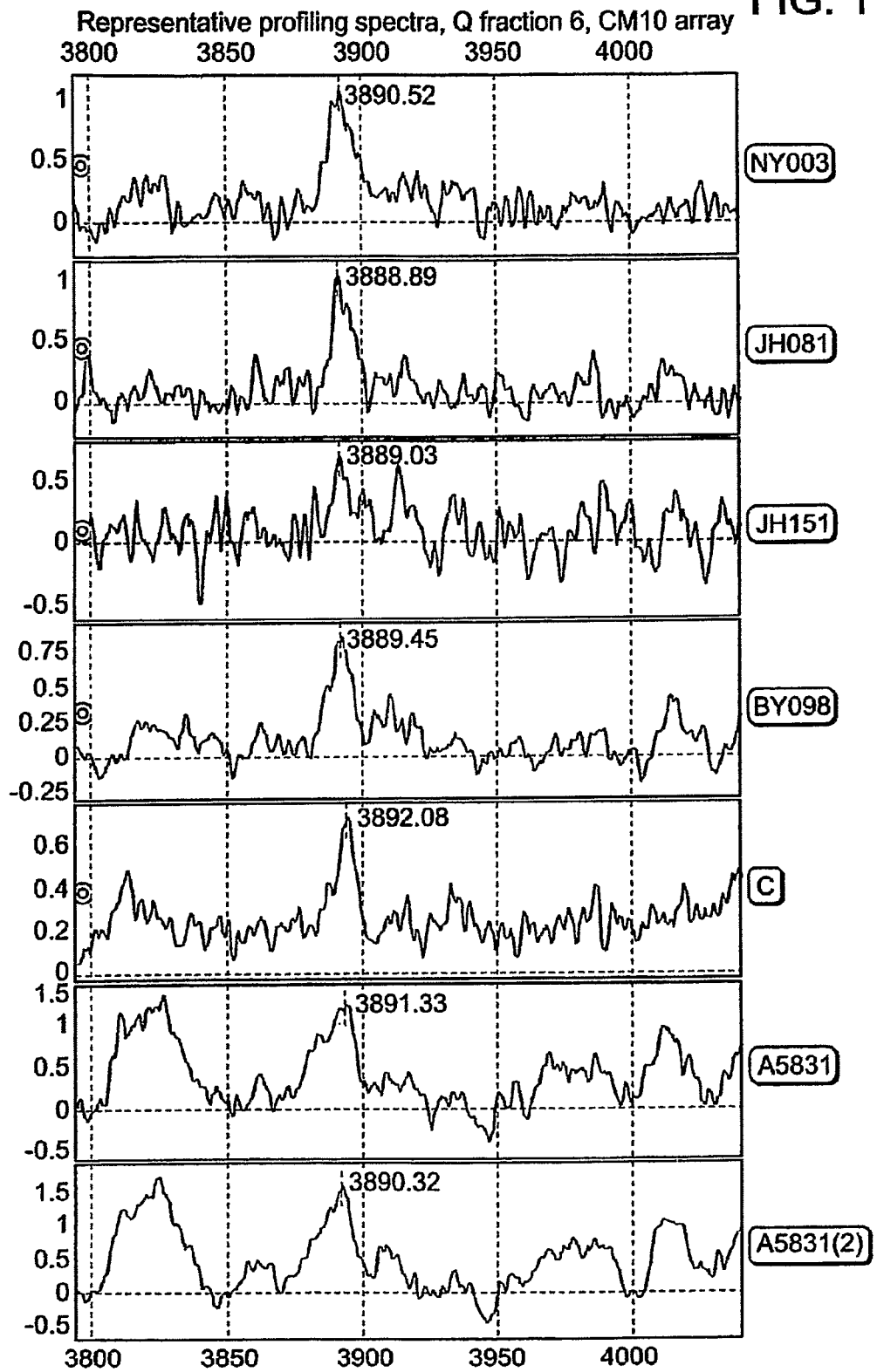
FIG. 1 shows representative profiling mass spectra for the PCI biomarker. In those Figures, the mass spectral peak of the specified marker is designated within the depicted spectra with the molecular weight.

A biomarker is an organic biomolecule which is differentially present in a sample taken from a subject of one phenotypic status (e.g. having a disease) as compared with another phenotypic status (e.g., not having the disease). A biomarker is differentially present between different phenotypic statuses if the mean or median expression level of the biomarker in the different groups is calculated to be statistically significant. Common tests for statistical significance include, among others, t-test, ANOVA, Kruskal-Wallis, Wilcoxon, Mann-Whitney and odds ratio. Biomarkers, alone or in combination, provide measures of relative risk that a subject belongs to one phenotypic status or another. Therefore, they are useful as markers for disease (diagnostics), therapeutic effectiveness of a drug (theranostics) and drug toxicity.

DEFINITIONS

Unless defined otherwise, all technical and scientific terms used herein have the meaning commonly understood by a person skilled in the art to which this invention belongs. The following references provide one of skill with a general definition of many of the terms used in this invention: Singleton et al., *Dictionary of Microbiology and Molecular Biology* (2nd ed. 1994); *The Cambridge Dictionary of Science and Technology* (Walker ed., 1988); *The Glossary of Genetics,* 5th Ed., R. Rieger et al. (eds.), Springer Verlag (1991); and Hale & Marham, *The Harper Collins Dictionary of Biology* (1991). As used herein, the following terms have the meanings ascribed to them unless specified otherwise.

As used herein, "diseases of the prostate" or "prostate disease," or "condition of the prostate," as used herein, refer to any disease or condition of the prostate including, but not limited to, benign prostatic hyperplasia (BPH), prostatitis, prostatic intraepithelial neoplasia (PIN) and cancer.

As used herein, "prostate cancer," as used herein, refers to any malignant disease of the prostate including, but not limited to, adenocarcinoma, small cell undifferentiated carcinoma and mucinous (colloid) cancer.

As used herein, the terms "metastatic prostate cancer" and "metastatic disease" mean prostate cancers which have spread to regional lymph nodes or to distant sites, and are meant to include stage D disease under the AUA system and stage TxNxM+under the TNM system. As is the case with locally advanced prostate cancer, surgery is generally not indicated for patients with metastatic disease, and hormonal (androgen ablation) therapy is the preferred treatment modality. Patients with metastatic prostate cancer eventually develop an androgen-refractory state within 12 to 18 months of treatment initiation, and approximately half of these patients die within 6 months thereafter. The most common site for prostate cancer metastasis is bone. Prostate cancer bone metastases are, on balance, characteristically osteoblastic rather than osteolytic (i.e., resulting in net bone formation). Bone metastases are found most frequently in the spine, followed by the femur, pelvis, rib cage, skull and humerus. Other common sites for metastasis include lymph nodes, lung, liver and brain. Metastatic prostate cancer is typically diagnosed by open or laparoscopic pelvic lymphadenectomy, whole body radionuclide scans, skeletal radiography, and/or bone lesion biopsy.

As used herein, the terms "locally advanced prostate cancer" and "locally advanced disease" mean prostate cancers which have extended through the prostate capsule, and are meant to include stage C disease under the American Urological Association (AUA) system, stage C1-C2 disease under the Whitmore-Jewett system, and stage T3-T4 and N+ disease under the TNM (tumor, node, metastasis) system. In general, surgery is not recommended for patients with locally advanced disease, and these patients have substantially less favorable outcomes compared to patients having clinically localized (organ-confined) prostate cancer. Locally advanced disease is clinically identified by palpable evidence of induration beyond the lateral border of the prostate or asymmetry or induration above the prostate base. Locally advanced prostate cancer is diagnosed pathologically following radical prostatectomy if the tumor invades or penetrates the prostatic capsule, extends into the surgical margin, or invades the seminal vesicles.

As used herein, "tumor stage" or "tumor progression" refers to the different clinical stages of the tumor. Clinical stages of a tumor are defined by various parameters which are well-established in the field of medicine. Some of the parameters include morphology, size of tumor, the degree in which it has metastasized through the patient's body and the like. The "Gleason Grading System" is a system of grading prostate cancer. The Gleason grading system assigns a grade to each of the two largest areas of cancer in the tissue samples. Grades range from 1 to 5, with 1 being the least aggressive and 5 the most aggressive. Grade 3 tumors, for example, seldom have metastases, but metastases are common with grade 4 or grade 5. The two grades are then added together to produce a Gleason score. A score of 2 to 4 is considered low grade; 5 through 7, intermediate grade; and 8 through 10, high grade. A tumor with a low Gleason score typically grows slowly enough that it may not pose a significant threat to the patient in his lifetime.

"Protein C inhibitor" (PCI), a plasma serine protease inhibitor, inhibits several proteases including the anticoagulant enzyme, activated protein C (APC), and the coagulation enzymes, thrombin and factor Xa and occurs at high concentration in seminal plasma.

"C4a" is a smaller fragment formed when C1s splits C4 into C4a and C4b. As an anaphylatoxin, C4a causes symptoms of immediate hypersensitivity but it has weaker activity than C3a or C5a.

"Gas phase ion spectrometer" refers to an apparatus that detects gas phase ions. Gas phase ion spectrometers include an ion source that supplies gas phase ions. Gas phase ion spectrometers include, for example, mass spectrometers, ion mobility spectrometers, and total ion current measuring devices. "Gas phase ion spectrometry" refers to the use of a gas phase ion spectrometer to detect gas phase ions.

"Mass spectrometer" refers to a gas phase ion spectrometer that measures a parameter that can be translated into mass-to-charge ratios of gas phase ions. Mass spectrometers generally include an ion source and a mass analyzer. Examples of mass spectrometers are time-of-flight, magnetic sector, quadrupole filter, ion trap, ion cyclotron resonance, electrostatic sector analyzer and hybrids of these. "Mass spectrometry" refers to the use of a mass spectrometer to detect gas phase ions.

"Laser desorption mass spectrometer" refers to a mass spectrometer that uses laser energy as a means to desorb, volatilize, and ionize an analyte.

"Tandem mass spectrometer" refers to any mass spectrometer that is capable of performing two successive stages of m/z-based discrimination or measurement of ions, including ions in an ion mixture. The phrase includes mass spectrometers having two mass analyzers that are capable of performing two successive stages of m/z-based discrimination or measurement of ions tandem-in-space. The phrase further includes mass spectrometers having a single mass analyzer that is capable of performing two successive stages of m/z-based discrimination or measurement of ions tandem-in-time. The phrase thus explicitly includes Qq-TOF mass spectrometers, ion trap mass spectrometers, ion trap-TOF mass spectrometers, TOF-TOF mass spectrometers, Fourier transform ion cyclotron resonance mass spectrometers, electrostatic sector-magnetic sector mass spectrometers, and combinations thereof.

"Mass analyzer" refers to a sub-assembly of a mass spectrometer that comprises means for measuring a parameter that can be translated into mass-to-charge ratios of gas phase ions. In a time-of-flight mass spectrometer the mass analyzer comprises an ion optic assembly, a flight tube and an ion detector.

"Ion source" refers to a sub-assembly of a gas phase ion spectrometer that provides gas phase ions. In one embodiment, the ion source provides ions through a desorption/ionization process. Such embodiments generally comprise a probe interface that positionally engages a probe in an interrogatable relationship to a source of ionizing energy (e.g., a laser desorption/ionization source) and in concurrent communication at atmospheric or subatmospheric pressure with a detector of a gas phase ion spectrometer.

Forms of ionizing energy for desorbing/ionizing an analyte from a solid phase include, for example: (1) laser energy; (2) fast atoms (used in fast atom bombardment); (3) high energy particles generated via beta decay of radionuclides (used in plasma desorption); and (4) primary ions generating secondary ions (used in secondary ion mass spectrometry). The preferred form of ionizing energy for solid phase analytes is a laser (used in laser desorption/ionization), in particular, nitrogen lasers, Nd-Yag lasers and other pulsed laser sources. "Fluence" refers to the energy delivered per unit area of interrogated image. A high fluence source, such as a laser, will deliver about 1 mJ/mm2 to 50 mJ/mm2. Typically, a sample is placed on the surface of a probe, the probe is engaged with the probe interface and the probe surface is struck with the ionizing energy. The energy desorbs analyte molecules from the surface into the gas phase and ionizes them.

Other forms of ionizing energy for analytes include, for example: (1) electrons that ionize gas phase neutrals; (2) strong electric field to induce ionization from gas phase, solid phase, or liquid phase neutrals; and (3) a source that applies a combination of ionization particles or electric fields with neutral chemicals to induce chemical ionization of solid phase, gas phase, and liquid phase neutrals.

"Solid support" refers to a solid material which can be derivatized with, or otherwise attached to, a capture reagent. Exemplary solid supports include probes, microtiter plates and chromatographic resins.

"Probe" in the context of this invention refers to a device adapted to engage a probe interface of a gas phase ion spectrometer (e.g., a mass spectrometer) and to present an analyte to ionizing energy for ionization and introduction into a gas phase ion spectrometer, such as a mass spectrometer. A "probe" will generally comprise a solid substrate (either flexible or rigid) comprising a sample presenting surface on which an analyte is presented to the source of ionizing energy.

"Surface-enhanced laser desorption/ionization" or "SELDI" refers to a method of desorption/ionization gas phase ion spectrometry (e.g., mass spectrometry) in which the analyte is captured on the surface of a SELDI probe that engages the probe interface of the gas phase ion spectrometer. In "SELDI MS," the gas phase ion spectrometer is a mass spectrometer. SELDI technology is described in, e.g., U.S. Pat. No. 5,719,060 (Hutchens and Yip) and U.S. Pat. No. 6,225,047 (Hutchens and Yip).

"Surface-Enhanced Affinity Capture" or "SEAC" is a version of SELDI that involves the use of probes comprising an absorbent surface (a "SEAC probe"). "Adsorbent surface" refers to a surface to which is bound an adsorbent (also called a "capture reagent" or an "affinity reagent"). An adsorbent is any material capable of binding an analyte (e.g., a target polypeptide or nucleic acid). "Chromatographic adsorbent" refers to a material typically used in chromatography. Chromatographic adsorbents include, for example, ion exchange materials, metal chelators (e.g., nitriloacetic acid or iminodiacetic acid), immobilized metal chelates, hydrophobic interaction adsorbents, hydrophilic interaction adsorbents, dyes, simple biomolecules (e.g., nucleotides, amino acids, simple sugars and fatty acids) and mixed mode adsorbents (e.g., hydrophobic attraction/electrostatic repulsion adsorbents). "Biospecific adsorbent" refers an adsorbent comprising a biomolecule, e.g., a nucleic acid molecule (e.g., an aptamer), a polypeptide, a polysaccharide, a lipid, a steroid or a conjugate of these (e.g., a glycoprotein, a lipoprotein, a glycolipid, a nucleic acid (e.g., DNA)-protein conjugate). In certain instances the biospecific adsorbent can be a macromolecular structure such as a multiprotein complex, a biological membrane or a virus. Examples of biospecific adsorbents are antibodies, receptor proteins and nucleic acids. Biospecific adsorbents typically have higher specificity for a target analyte than chromatographic adsorbents. Further examples of adsorbents for use in SELDI can be found in U.S. Pat. No. 6,225,047 (Hutchens and Yip, "Use of retentate chromatography to generate difference maps," May 1, 2001).

In some embodiments, a SEAC probe is provided as a pre-activated surface which can be modified to provide an adsorbent of choice. For example, certain probes are provided with a reactive moiety that is capable of binding a biological molecule through a covalent bond. Epoxide and carbodiimidizole are useful reactive moieties to covalently bind biospecific adsorbents such as antibodies or cellular receptors.

"Adsorption" refers to detectable non-covalent binding of an analyte to an adsorbent or capture reagent.

"Surface-Enhanced Neat Desorption" or "SEND" is a version of SELDI that involves the use of probes comprising energy absorbing molecules chemically bound to the probe surface. ("SEND probe.") "Energy absorbing molecules" ("EAM") refer to molecules that are capable of absorbing energy from a laser desorption/ionization source and thereafter contributing to desorption and ionization of analyte molecules in contact therewith. The phrase includes molecules used in MALDI, frequently referred to as "matrix", and explicitly includes cinnamic acid derivatives, sinapinic acid ("SPA"), cyano-hydroxy-cinnamic acid ("CHCA") and dihydroxybenzoic acid, ferulic acid, hydroxyacetophenone derivatives, as well as others. It also includes EAMs used in SELDI. SEND is further described in U.S. Pat. No. 5,719,060 and U.S. patent application 60/408,255, filed Sep. 4, 2002 (Kitagawa, "Monomers And Polymers Having Energy Absorbing Moieties Of Use In Desorption/Ionization Of Analytes").

"Surface-Enhanced Photolabile Attachment and Release" or "SEPAR" is a version of SELDI that involves the use of probes having moieties attached to the surface that can covalently bind an analyte, and then release the analyte through breaking a photolabile bond in the moiety after exposure to light e.g., laser light. SEPAR is further described in U.S. Pat. No. 5,719,060.

"Eluant" or "wash solution" refers to an agent, typically a solution, which is used to affect or modify adsorption of an analyte to an adsorbent surface and/or remove unbound materials from the surface. The elution characteristics of an eluant can depend, for example, on pH, ionic strength, hydrophobicity, degree of chaotropism, detergent strength and temperature.

"Analyte" refers to any component of a sample that is desired to be detected. The term can refer to a single component or a plurality of components in the sample.

The "complexity" of a sample adsorbed to an adsorption surface of an affinity capture probe means the number of different protein species that are adsorbed.

"Molecular binding partners" and "specific binding partners" refer to pairs of molecules, typically pairs of biomolecules that exhibit specific binding. Molecular binding partners include, without limitation, receptor and ligand, antibody and antigen, biotin and avidin, and biotin and streptavidin.

"Monitoring" refers to recording changes in a continuously varying parameter.

"Biochip" refers to a solid substrate having a generally planar surface to which an adsorbent is attached. Frequently, the surface of the biochip comprises a plurality of addressable locations, each of which location has the adsorbent bound there. Biochips can be adapted to engage a probe interface and, therefore, function as probes.

"Protein biochip" refers to a biochip adapted for the capture of polypeptides. Many protein biochips are described in the art. These include, for example, protein biochips produced by Ciphergen Biosystems (Fremont, Calif.), Packard BioScience Company (Meriden Conn.), Zyomyx (Hayward, Calif.) and Phylos (Lexington, Mass.). Examples of such protein biochips are described in the following patents or patent applications: U.S. Pat. No. 6,225,047 (Hutchens and Yip, "Use of retentate chromatography to generate difference maps," May 1, 2001); International publication WO 99/51773 (Kuimelis and Wagner, "Addressable protein arrays," Oct. 14, 1999); U.S. Pat. No. 6,329,209 (Wagner et al., "Arrays of protein-capture agents and methods of use thereof," Dec. 11, 2001) and International publication WO 00/56934 (Englert et al., "Continuous porous matrix arrays," Sep. 28, 2000).

Protein biochips produced by Ciphergen Biosystems comprise surfaces having chromatographic or biospecific adsorbents attached thereto at addressable locations. Ciphergen ProteinChip® arrays include NP20, H4, H50, SAX-2, WCX-2, CM-10, IMAC-3, IMAC-30, LSAX-30, LWCX-30, IMAC-40, PS-10, PS-20 and PG-20. These protein biochips comprise an aluminum substrate in the form of a strip. The surface of the strip is coated with silicon dioxide.

In the case of the NP-20 biochip, silicon oxide functions as a hydrophilic adsorbent to capture hydrophilic proteins.

H4, H50, SAX-2, WCX-2, CM-10, IMAC-3, IMAC-30, PS-10 and PS-20 biochips further comprise a functionalized, cross-linked polymer in the form of a hydrogel physically attached to the surface of the biochip or covalently attached through a silane to the surface of the biochip. The H4 biochip has isopropyl functionalities for hydrophobic binding. The H50 biochip has nonylphenoxy-poly(ethylene glycol)methacrylate for hydrophobic binding. The SAX-2 biochip has quaternary ammonium functionalities for anion exchange. The WCX-2 and CM-10 biochips have carboxylate functionalities for cation exchange. The IMAC-3 and IMAC-30 biochips have nitriloacetic acid functionalities that adsorb transition metal ions, such as $Cu^{++}$ and $N^{++}$, by chelation. These immobilized metal ions allow adsorption of peptide and proteins by coordinate bonding. The PS-10 biochip has carboimidizole functional groups that can react with groups on proteins for covalent binding. The PS-20 biochip has epoxide functional groups for covalent binding with proteins. The PS-series biochips are useful for binding biospecific adsorbents, such as antibodies, receptors, lectins, heparin, Protein A, biotin/streptavidin and the like, to chip surfaces where they function to specifically capture analytes from a sample. The PG-20 biochip is a PS-20 chip to which Protein G is attached.

The LSAX-30 (anion exchange), LWCX-30 (cation exchange) and IMAC-40 (metal chelate) biochips have functionalized latex beads on their surfaces. Such biochips are further described in: WO 00/66265 (Rich et al., "Probes for a Gas Phase Ion Spectrometer," Nov. 9, 2000); WO 00/67293 (Beecher et al., "Sample Holder with Hydrophobic Coating for Gas Phase Mass Spectrometer," Nov. 9, 2000); U.S. patent application US20030032043A1 (Pohl and Papanu, "Latex Based Adsorbent Chip," Jul. 16, 2002) and U.S. patent application 60/350,110 (Um et al., "Hydrophobic Surface Chip," Nov. 8, 2001).

Upon capture on a biochip, analytes can be detected by a variety of detection methods selected from, for example, a gas phase ion spectrometry method, an optical method, an electrochemical method, atomic force microscopy and a radio frequency method. Gas phase ion spectrometry methods are described herein. Of particular interest is the use of mass spectrometry and, in particular, SELDI. Optical methods include, for example, detection of fluorescence, luminescence, chemiluminescence, absorbance, reflectance, transmittance, birefringence or refractive index (e.g., surface plasmon resonance, ellipsometry, a resonant mirror method, a grating coupler waveguide method or interferometry). Optical methods include microscopy (both confocal and non-confocal), imaging methods and non-imaging methods. Immunoassays in various formats (e.g., ELISA) are popular methods for detection of analytes captured on a solid phase. Electrochemical methods include voltametry and amperometry methods. Radio frequency methods include multipolar resonance spectroscopy.

"Marker" in the context of the present invention refers to a polypeptide (of a particular apparent molecular weight), which is differentially present in a sample taken from patients having human cancer as compared to a comparable sample taken from control subjects (e.g., a person with a negative diagnosis or undetectable cancer, normal or healthy subject). The term "biomarker" is used interchangeably with the term "marker."

The term "measuring" means methods which include detecting the presence or absence of marker(s) in the sample, quantifying the amount of marker(s) in the sample, and/or qualifying the type of biomarker. Measuring can be accomplished by methods known in the art and those further described herein, including but not limited to SELDI and immunoassay. Any suitable methods can be used to detect and measure one or more of the markers described herein. These methods include, without limitation, mass spectrometry (e.g., laser desorption/ionization mass spectrometry), fluorescence (e.g. sandwich immunoassay), surface plasmon resonance, ellipsometry and atomic force microscopy.

"Detect" refers to identifying the presence, absence or amount of the object to be detected.

The phrase "differentially present" refers to differences in the quantity and/or the frequency of a marker present in a sample taken from patients having human cancer as compared to a control subject. For example, some markers described herein are present at an elevated level in samples of cancer patients compared to samples from control subjects. In contrast, other markers described herein are present at a decreased level in samples of cancer patients compared to samples from control subjects. Furthermore, a marker can be a polypeptide, which is detected at a higher frequency or at a lower frequency in samples of human cancer patients compared to samples of control subjects. A marker can be differentially present in terms of quantity, frequency or both.

A polypeptide is differentially present between two samples if the amount of the polypeptide in one sample is statistically significantly different from the amount of the polypeptide in the other sample. For example, a polypeptide is differentially present between the two samples if it is present at least about 120%, at least about 130%, at least about 150%, at least about 180%, at least about 200%, at least about 300%, at least about 500%, at least about 700%, at least about 900%, or at least about 1000% greater than it is present in the other sample, or if it is detectable in one sample and not detectable in the other.

Alternatively or additionally, a polypeptide is differentially present between two sets of samples if the frequency of detecting the polypeptide in the prostate cancer patients' samples is statistically significantly higher or lower than in the control samples. For example, a polypeptide is differentially present between the two sets of samples if it is detected at least about 120%, at least about 130%, at least about 150%, at least about 180%, at least about 200%, at least about 300%, at least about 500%, at least about 700%, at least about 900%, or at least about 1000% more frequently or less frequently observed in one set of samples than the other set of samples.

"Diagnostic" means identifying the presence or nature of a pathologic condition, i.e., prostate cancer. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

A "test amount" of a marker refers to an amount of a marker present in a sample being tested. A test amount can be either in absolute amount (e.g., µg/ml) or a relative amount (e.g., relative intensity of signals).

A "diagnostic amount" of a marker refers to an amount of a marker in a subject's sample that is consistent with a diagnosis of prostate cancer. A diagnostic amount can be either in absolute amount (e.g., µg/ml) or a relative amount (e.g. relative intensity of signals).

A "control amount" of a marker can be any amount or a range of amount, which is to be compared against a test amount of a marker. For example, a control amount of a marker can be the amount of a marker in a person without prostate cancer. A control amount can be either in absolute amount (e.g., µg/ml) or a relative amount (e.g., relative intensity of signals).

As used herein, the term "sensitivity" is the percentage of patients with a particular disease. For example, in the PCa/HC group, the biomarkers of the invention have a sensitivity of about 98%. The panel of biomarkers correctly classified 101 out of 103 prostate cancer patients as having prostate cancer, ie. 101/103=98%.

As used herein, the term "specificity" is the percentage of patients correctly identified as having a particular disease i.e. normal or healthy subjects. For example, the specificity is calculated as the number of subjects with a particular disease as compared to normal healthy subjects.

The terms "polypeptide," "peptide" and "protein" are used interchangeably herein to refer to a polymer of amino acid residues. The terms apply to amino acid polymers in which one or more amino acid residue is an analog or mimetic of a corresponding naturally occurring amino acid, as well as to naturally occurring amino acid polymers. Polypeptides can be modified, e.g., by the addition of carbohydrate residues to form glycoproteins. The terms "polypeptide," "peptide" and "protein" include glycoproteins, as well as non-glycoproteins.

"Immunoassay" is an assay that uses an antibody to specifically bind an antigen (e.g., a marker). The immunoassay is characterized by the use of specific binding properties of a particular antibody to isolate, target, and/or quantify the antigen.

"Antibody" refers to a polypeptide ligand substantially encoded by an immunoglobulin gene or immunoglobulin genes, or fragments thereof, which specifically binds and recognizes an epitope (e.g., an antigen). The recognized immunoglobulin genes include the kappa and lambda light chain constant region genes, the alpha, gamma, delta, epsilon and mu heavy chain constant region genes, and the myriad immunoglobulin variable region genes. Antibodies exist, e.g., as intact immunoglobulins or as a number of well-characterized fragments produced by digestion with various peptidases. This includes, e.g., Fab' and F(ab)'$_2$ fragments. The term "antibody," as used herein, also includes antibody fragments either produced by the modification of whole antibodies or those synthesized de novo using recombinant DNA methodologies. It also includes polyclonal antibodies, monoclonal antibodies, chimeric antibodies, humanized antibodies, or single chain antibodies. "Fc" portion of an antibody refers to that portion of an immunoglobulin heavy chain that comprises one or more heavy chain constant region domains, $CH_1$, $CH_2$ and $CH_3$, but does not include the heavy chain variable region.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, polyclonal antibodies raised to marker "X" from specific species such as rat, mouse, or human can be selected to obtain only those polyclonal antibodies that are specifically immunoreactive with marker "X" and not with other proteins, except for polymorphic variants and alleles of marker "X". This selection may be achieved by subtracting out antibodies that cross-react with marker "X" molecules from other species. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988), for a description of immunoassay formats and conditions that can be used to determine specific immunoreactivity). Typically a specific or selective reaction will be at least twice background signal or noise and more typically more than 10 to 100 times background.

"Managing subject treatment" refers to the behavior of the clinician or physician subsequent to the determination of prostate cancer status. For example, if the result of the methods of the present invention is inconclusive or there is reason that confirmation of status is necessary, the physician may order more tests. Alternatively, if the status indicates that surgery is appropriate, the physician may schedule the patient for surgery. Likewise, if the status is negative, e.g., late stage prostate cancer or if the status is acute, no further action may be warranted. Furthermore, if the results show that treatment has been successful, no further management may be necessary.

2. Biomarkers for Prostate Cancer 2.1. Biomarkers

This invention provides a polypeptide-based biomarker, PCI, that is differentially present in subjects having Prostate Cancer, in particular, Prostate Cancer versus normal (non-Prostate Cancer). The biomarker is characterized by molecular weight, mass-to-charge ratio as determined by mass spectrometry, by the shape of their spectral peak in time-of-flight mass spectrometry and by their binding characteristics to adsorbent surfaces. These characteristics provide one method to determine whether a particular detected biomolecule is a biomarker of this invention. These characteristics represent inherent characteristics of the biomolecules and not process limitations in the manner in which the biomolecules are discriminated.

The biomarker was discovered using SELDI technology employing ProteinChip arrays from Ciphergen Biosystems, Inc. (Fremont, Calif.) ("Ciphergen"). Pooled serum samples were collected from subjects diagnosed with Prostate Cancer and subjects diagnosed as normal. The samples were fractionated by anion exchange chromatography. Fractionated samples were applied to SELDI biochips and spectra of polypeptides in the samples were generated by time-of-flight mass spectrometry on a Ciphergen PBSII mass spectrometer. The spectra thus obtained were analyzed by Ciphergen Express™ Data Manager Software with Biomarker Wizard and Biomarker Pattern Software from Ciphergen Biosystems, Inc. The mass spectra for each group were subjected to scatter plot analysis. A Mann-Whitney test analysis was employed to compare Prostate Cancer and control groups for each protein cluster in the scatter plot, and proteins were selected that differed significantly (p<0.0001) between the two groups. This method is described in more detail in the Example Section.

The biomarker thus discovered is PCI. The "ProteinChip assay" column refers to chromatographic fraction in which the biomarker is found, the type of biochip to which the biomarker binds and the wash conditions.

TABLE 1

| Marker | P-Value | Up or down regulated in Prostate Cancer | ProteinChip ® assay |
|---|---|---|---|
| PCI (3890 DA) | <0.0001 | Up | CM10 |

The biomarker of this invention is characterized by their mass-to-charge ratio as determined by mass spectrometry. The mass-to-charge ratios are determined from mass spectra generated on a Ciphergen Biosystems, Inc. PBS II mass spectrometer. This instrument has a mass accuracy of about +/−0.15 percent. Additionally, the instrument has a mass resolution of about 400 to 1000 m/dm, where m is mass and dm is the mass spectral peak width at 0.5 peak height. The mass-to-charge ratio of the biomarkers was determined using Biomarker Wizard™ software (Ciphergen Biosystems, Inc.). Biomarker Wizard assigns a mass-to-charge ratio to a biomarker by clustering the mass-to-charge ratios of the same peaks from all the spectra analyzed, as determined by the PBSII, taking the maximum and minimum mass-to-charge-ratio in the cluster, and dividing by two. Accordingly, the masses provided reflect these specifications.

The biomarker of this invention is further characterized by the shape of their spectral peak in time-of-flight mass spectrometry. Mass spectra showing peaks representing the biomarkers are presented in FIG. 8.

The biomarker of this invention is further characterized by their binding properties on chromatographic surfaces. Most biomarkers bind to cation exchange adsorbents (e.g., the Ciphergen® WCX ProteinChip® array) after washing with 100 mM sodium acetate at pH 4.

Because the biomarker of this invention is characterized by mass-to-charge ratio, binding properties and spectral shape, they can be detected by mass spectrometry without knowing their specific identity. However, if desired, biomarkers whose identity is not determined can be identified by, for example, determining the amino acid sequence of the polypeptides. For example, a biomarker can be peptide-mapped with a number of enzymes, such as trypsin or V8 protease, and the molecular weights of the digestion fragments can be used to search databases for sequences that match the molecular weights of the digestion fragments generated by the various enzymes. Alternatively, protein biomarkers can be sequenced using tandem MS technology. In this method, the protein is isolated by, for example, gel electrophoresis. A band containing the biomarker is cut out and the protein is subject to protease digestion. Individual protein fragments are separated by a first mass spectrometer. The fragment is then subjected to collision-induced cooling, which fragments the peptide and produces a polypeptide ladder. A polypeptide ladder is then analyzed by the second mass spectrometer of the tandem MS. The difference in masses of the members of the polypeptide ladder identifies the amino acids in the sequence. An entire protein can be sequenced this way, or a sequence fragment can be subjected to database mining to find identity candidates.

The preferred biological source for detection of the biomarkers is serum. However, in other embodiments, the biomarkers can be detected in plasma or urine.

The biomarker of this invention is a polypeptide. Accordingly, this invention provides this polypeptide in isolated form. The biomarker can be isolated from biological fluids, such as urine or serum. It can be isolated by any method known in the art, based on both their mass and their binding characteristics. For example, a sample comprising the polypeptide can be subject to chromatographic fractionation, as described herein, and subject to further separation by, e.g., acrylamide gel electrophoresis. Knowledge of the identity of the biomarker also allows their isolation by immunoaffinity chromatography.

3. Biomarkers and Different Forms of a Protein

Proteins frequently exist in a sample in a plurality of different forms. These forms can result from either or both of pre- and post-translational modification. Pre-translational modified forms include allelic variants, splice variants and RNA editing forms. Post-translationally modified forms include forms resulting from proteolytic cleavage (e.g., cleavage of a signal sequence or fragments of a parent protein), glycosylation, phosphorylation, lipidation, oxidation, methylation, cysteinylation, sulphonation and acetylation.

When detecting or measuring a protein in a sample, the ability to differentiate between different forms of a protein depends upon the nature of the difference and the method used to detect or measure. For example, an immunoassay using a monoclonal antibody will detect all forms of a protein containing the eptiope and will not distinguish between them. However, a sandwich immunoassay that uses two antibodies directed against different epitopes on a protein will detect all forms of the protein that contain both epitopes and will not detect those forms that contain only one of the epitopes.

In diagnostic assays, the inability to distinguish different forms of a protein has little impact when the forms detected by the particular method used are equally good biomarkers as any particular form. However, when a particular form (or a subset of particular forms) of a protein is a better biomarker than the collection of different forms detected together by a particular method, the power of the assay may suffer. In this case, it is useful to employ an assay method that distinguishes between forms of a protein and that specifically detects and measures a desired form or forms of the protein. Distinguishing different forms of an analyte or specifically detecting a particular form of an analyte is referred to as "resolving" the analyte.

Mass spectrometry is a particularly powerful methodology to resolve different forms of a protein because the different forms typically have different masses that can be resolved by mass spectrometry. Accordingly, if one form of a protein is a superior biomarker for a disease than another form of the biomarker, mass spectrometry may be able to specifically detect and measure the useful form where traditional immunoassay fails to distinguish the forms and fails to specifically detect to useful biomarker.

One useful methodology combines mass spectrometry with immunoassay. First, a biospecific capture reagent (e.g., an antibody, aptamer or Affibody that recognizes the biomarker and other forms of it) is used to capture the biomarker of interest. Preferably, the biospecific capture reagent is bound to a solid phase, such as a bead, a plate, a membrane or an array. After unbound materials are washed away, the captured analytes are detected and/or measured by mass spectrometry. (This method also will also result in the capture of protein interactors that are bound to the proteins or that are otherwise recognized by antibodies and that, themselves, can be biomarkers.) Various forms of mass spectrometry are useful for detecting the protein forms, including laser desorption approaches, such as traditional MALDI or SELDI, and electrospray ionization.

Thus, when reference is made herein to detecting a particular protein or to measuring the amount of a particular protein, it means detecting and measuring the protein with or without resolving various forms of protein. For example, the step of "CPI" includes measuring CPI by means that do not differentiate between various forms of the protein in a sample as well as by means that differentiate some forms from other forms or that measure a specific form of the protein.

4. Detection of Biomarkers for Prostate Cancer

The biomarkers of this invention can be detected by any suitable method. Detection paradigms that can be employed to this end include optical methods, electrochemical methods (voltametry and amperometry techniques), atomic force microscopy, and radio frequency methods, e.g., multipolar resonance spectroscopy. Illustrative of optical methods, in addition to microscopy, both confocal and non-confocal, are detection of fluorescence, luminescence, chemiluminescence, absorbance, reflectance, transmittance, and birefringence or refractive index (e.g., surface plasmon resonance, ellipsometry, a resonant mirror method, a grating coupler waveguide method or interferometry).

In one embodiment, a sample is analyzed by means of a biochip. Biochips generally comprise solid substrates and have a generally planar surface, to which a capture reagent (also called an adsorbent or affinity reagent) is attached. Frequently, the surface of a biochip comprises a plurality of addressable locations, each of which has the capture reagent bound there.

Protein biochips are biochips adapted for the capture of polypeptides. Many protein biochips are described in the art. These include, for example, protein biochips produced by Ciphergen Biosystems, Inc. (Fremont, Calif.), Zyomyx (Hayward, Calif.), Invitrogen (Carlsbad, Calif.), Biacore (Uppsala, Sweden) and Procognia (Berkshire, UK). Examples of such protein biochips are described in the following patents or published patent applications: U.S. Pat. No. 6,225,047 (Hutchens & Yip); U.S. Pat. No. 6,537,749 Kuimelis and Wagner); U.S. Pat. No. 6,329,209 (Wagner et al.); PCT International Publication No. WO 00/56934 (Englert et al.); PCT International Publication No. WO 03/048768 (Boutell et al.) and U.S. Pat. No. 5,242,828 (Bergstrom et al.).

4.1. Detection by Mass Spectrometry

In a preferred embodiment, the biomarker of this invention is detected by mass spectrometry, a method that employs a mass spectrometer to detect gas phase ions. Examples of mass spectrometers are time-of-flight, magnetic sector, quadrupole filter, ion trap, ion cyclotron resonance, electrostatic sector analyzer and hybrids of these.

In a further preferred method, the mass spectrometer is a laser desorption/ionization mass spectrometer. In laser desorption/ionization mass spectrometry, the analytes are placed on the surface of a mass spectrometry probe, a device adapted to engage a probe interface of the mass spectrometer and to present an analyte to ionizing energy for ionization and introduction into a mass spectrometer. A laser desorption mass spectrometer employs laser energy, typically from an ultraviolet laser, but also from an infrared laser, to desorb analytes from a surface, to volatilize and ionize them and make them available to the ion optics of the mass spectrometer.

SELDI

A preferred mass spectrometric technique for use in the invention is "Surface Enhanced Laser Desorption and Ionization" or "SELDI," as described, for example, in U.S. Pat. No. 5,719,060 and No. 6,225,047, both to Hutchens and Yip. This refers to a method of desorption/ionization gas phase ion spectrometry (e.g. mass spectrometry) in which an analyte (here, one or more of the biomarkers) is captured on the surface of a SELDI mass spectrometry probe. There are several versions of SELDI.

One version of SELDI is called "affinity capture mass spectrometry." It also is called "Surface-Enhanced Affinity Capture" or "SEAC". This version involves the use of probes that have a material on the probe surface that captures analytes through a non-covalent affinity interaction (adsorption) between the material and the analyte. The material is variously called an "adsorbent," a "capture reagent," an "affinity reagent" or a "binding moiety." Such probes can be referred to as "affinity capture probes" and as having an "adsorbent surface." The capture reagent can be any material capable of binding an analyte. The capture reagent is attached to the probe surface by physisorption or chemisorption. In certain embodiments the probes have the capture reagent already attached to the surface. In other embodiments, the probes are pre-activated and include a reactive moiety that is capable of binding the capture reagent, e.g., through a reaction forming a covalent or coordinate covalent bond. Epoxide and acyl-imidizole are useful reactive moieties to covalently bind polypeptide capture reagents such as antibodies or cellular receptors. Nitrilotriacetic acid and iminodiacetic acid are useful reactive moieties that function as chelating agents to bind metal ions that interact non-covalently with histidine containing peptides. Adsorbents are generally classified as chromatographic adsorbents and biospecific adsorbents.

"Chromatographic adsorbent" refers to an adsorbent material typically used in chromatography. Chromatographic adsorbents include, for example, ion exchange materials, metal chelators (e.g., nitrilotriacetic acid or iminodiacetic acid), immobilized metal chelates, hydrophobic interaction adsorbents, hydrophilic interaction adsorbents, dyes, simple biomolecules (e.g., nucleotides, amino acids, simple sugars and fatty acids) and mixed mode adsorbents (e.g., hydrophobic attraction/electrostatic repulsion adsorbents).

"Biospecific adsorbent" refers to an adsorbent comprising a biomolecule, e.g., a nucleic acid molecule (e.g., an aptamer), a polypeptide, a polysaccharide, a lipid, a steroid or a conjugate of these (e.g., a glycoprotein, a lipoprotein, a glycolipid, a nucleic acid (e.g., DNA)-protein conjugate). In certain instances, the biospecific adsorbent can be a macromolecular structure such as a multiprotein complex, a biological membrane or a virus. Examples of biospecific adsorbents are antibodies, receptor proteins and nucleic acids. Biospecific adsorbents typically have higher specificity for a target analyte than chromatographic adsorbents. Further examples of adsorbents for use in SELDI can be found in U.S. Pat. No. 6,225,047. A "bioselective adsorbent" refers to an adsorbent that binds to an analyte with an affinity of at least $10^{-8}$ M.

Protein biochips produced by Ciphergen Biosystems, Inc. comprise surfaces having chromatographic or biospecific adsorbents attached thereto at addressable locations. Ciphergen ProteinChip® arrays include NP20 (hydrophilic); H4 and H50 (hydrophobic); SAX-2, Q-10 and LSAX-30 (anion exchange); WCX-2, CM-10 and LWCX-30 (cation exchange); IMAC-3, MAC-30 and IMAC 40 (metal chelate); and PS-10, PS-20 (reactive surface with acyl-imidizole, epoxide) and PG-20 (protein G coupled through acyl-imidizole). Hydrophobic ProteinChip arrays have isopropyl or nonylphenoxy-poly(ethylene glycol)methacrylate functionalities. Anion exchange ProteinChip arrays have quaternary ammonium functionalities. Cation exchange ProteinChip arrays have carboxylate functionalities. Immobilized metal chelate ProteinChip arrays have nitrilotriacetic acid functionalities that adsorb transition metal ions, such as copper, nickel, zinc, and gallium, by chelation. Preactivated ProteinChip arrays have acyl-imidizole or epoxide functional groups that can react with groups on proteins for covalent binding.

Such biochips are further described in: U.S. Pat. No. 6,579,719 (Hutchens and Yip, "Retentate Chromatography," Jun. 17, 2003); U.S. Pat. No. 6,897,072 (Rich et al., "Probes for a Gas Phase Ion Spectrometer," May 24, 2005); U.S. Pat. No. 6,555,813 (Beecher et al., "Sample Holder with Hydrophobic Coating for Gas Phase Mass Spectrometer," Apr. 29, 2003); U.S. Patent Publication No. U.S. 2003-0032043 A1 (Pohl and Papanu, "Latex Based Adsorbent Chip," Jul. 16, 2002); and PCT International Publication No. WO 03/040700 (Um et al., "Hydrophobic Surface Chip," May 15, 2003); U.S. Patent Application Publication No. US 2003/-0218130 A1 (Boschetti et al., "Biochips With Surfaces Coated With Polysaccharide-Based Hydrogels," Apr. 14, 2003) and U.S. Pat. No. 7,045,366 (Huang et al., "Photocrosslinked Hydrogel Blend Surface Coatings" May 16, 2006).

In general, a probe with an adsorbent surface is contacted with the sample for a period of time sufficient to allow the biomarker or biomarkers that may be present in the sample to bind to the adsorbent. After an incubation period, the substrate is washed to remove unbound material. Any suitable washing solutions can be used; preferably, aqueous solutions are employed. The extent to which molecules remain bound can be manipulated by adjusting the stringency of the wash. The elution characteristics of a wash solution can depend, for example, on pH, ionic strength, hydrophobicity, degree of chaotropism, detergent strength, and temperature. Unless the probe has both SEAC and SEND properties (as described herein), an energy absorbing molecule then is applied to the substrate with the bound biomarkers.

The biomarkers bound to the substrates are detected in a gas phase ion spectrometer such as a time-of-flight mass spectrometer. The biomarkers are ionized by an ionization source such as a laser, the generated ions are collected by an ion optic assembly, and then a mass analyzer disperses and analyzes the passing ions. The detector then translates information of the detected ions into mass-to-charge ratios. Detection of a biomarker typically will involve detection of signal intensity. Thus, both the quantity and mass of the biomarker can be determined.

Another version of SELDI is Surface-Enhanced Neat Desorption (SEND), which involves the use of probes comprising energy absorbing molecules that are chemically bound to the probe surface ("SEND probe"). The phrase "energy absorbing molecules" (EAM) denotes molecules that are capable of absorbing energy from a laser desorption/ionization source and, thereafter, contribute to desorption and ionization of analyte molecules in contact therewith. The EAM category includes molecules used in MALDI, frequently referred to as "matrix," and is exemplified by cinnamic acid derivatives, sinapinic acid (SPA), cyano-hydroxy-cinnamic acid (CHCA) and dihydroxybenzoic acid, ferulic acid, and hydroxyacetophenone derivatives. In certain embodiments, the energy absorbing molecule is incorporated into a linear or cross-linked polymer, e.g., a polymethacrylate. For example, the composition can be a co-polymer of α-cyano-4-methacryloyloxycinnamic acid and acrylate. In another embodiment, the composition is a co-polymer of α-cyano-4-methacryloyloxycinnamic acid, acrylate and 3-(tri-ethoxy)silyl propyl methacrylate. In another embodiment, the composition is a co-polymer of α-cyano-4-methacryloyloxycinnamic acid and octadecylmethacrylate "C18 SEND"). SEND is further described in U.S. Pat. No. 6,124,137 and PCT International Publication No. WO 03/64594 (Kitagawa, "Monomers And Polymers Having Energy Absorbing Moieties Of Use In Desorption/Ionization Of Analytes," Aug. 7, 2003).

SEAC/SEND is a version of SELDI in which both a capture reagent and an energy absorbing molecule are attached to the sample presenting surface. SEAC/SEND probes therefore allow the capture of analytes through affinity capture and ionization/desorption without the need to apply external matrix. The C18 SEND biochip is a version of SEAC/SEND, comprising a C18 moiety which functions as a capture reagent, and a CHCA moiety which functions as an energy absorbing moiety.

Another version of SELDI, called Surface-Enhanced Photolabile Attachment and Release (SEPAR), involves the use of probes having moieties attached to the surface that can covalently bind an analyte, and then release the analyte through breaking a photolabile bond in the moiety after exposure to light, e.g., to laser light (see, U.S. Pat. No. 5,719,060). SEPAR and other forms of SELDI are readily adapted to detecting a biomarker or biomarker profile, pursuant to the present invention.

Other Mass Spectrometry Methods

In another mass spectrometry method, the biomarkers can be first captured on a chromatographic resin having chromatographic properties that bind the biomarkers. In the present example, this could include a variety of methods. For example, one could capture the biomarkers on a cation exchange resin, such as CM Ceramic HyperD F resin, wash the resin, elute the biomarkers and detect by MALDI. Alternatively, this method could be preceded by fractionating the sample on an anion exchange resin before application to the cation exchange resin. In another alternative, one could fractionate on an anion exchange resin and detect by MALDI directly. In yet another method, one could capture the biomarkers on an immuno-chromatographic resin that comprises antibodies that bind the biomarkers, wash the resin to remove unbound material, elute the biomarkers from the resin and detect the eluted biomarkers by MALDI or by SELDI.

Data Analysis

Analysis of analytes by time-of-flight mass spectrometry generates a time-of-flight spectrum. The time-of-flight spectrum ultimately analyzed typically does not represent the signal from a single pulse of ionizing energy against a sample, but rather the sum of signals from a number of pulses. This reduces noise and increases dynamic range. This time-of-flight data is then subject to data processing. In Ciphergen's ProteinChip® software, data processing typically includes TOF-to-M/Z transformation to generate a mass spectrum, baseline subtraction to eliminate instrument offsets and high frequency noise filtering to reduce high frequency noise.

Data generated by desorption and detection of biomarkers can be analyzed with the use of a programmable digital computer. The computer program analyzes the data to indicate the number of biomarkers detected, and optionally the strength of the signal and the determined molecular mass for each biomarker detected. Data analysis can include steps of determining signal strength of a biomarker and removing data deviating from a predetermined statistical distribution. For example, the observed peaks can be normalized, by calculating the height of each peak relative to some reference. The reference can be background noise generated by the instrument and chemicals such as the energy absorbing molecule which is set at zero in the scale.

The computer can transform the resulting data into various formats for display. The standard spectrum can be displayed, but in one useful format only the peak height and mass information are retained from the spectrum view, yielding a cleaner image and enabling biomarkers with nearly identical molecular weights to be more easily seen. In another useful format, two or more spectra are compared, conveniently highlighting unique biomarkers and biomarkers that are up- or down-regulated between samples. Using any of these formats, one can readily determine whether a particular biomarker is present in a sample.

Analysis generally involves the identification of peaks in the spectrum that represent signal from an analyte. Peak selection can be done visually, but software is available, as part of Ciphergen's ProteinChip® software package, that can automate the detection of peaks. In general, this software functions by identifying signals having a signal-to-noise ratio above a selected threshold and labeling the mass of the peak at the centroid of the peak signal. In one useful application, many spectra are compared to identify identical peaks present in some selected percentage of the mass spectra. One version of this software clusters all peaks appearing in the various spectra within a defined mass range, and assigns a mass (M/Z) to all the peaks that are near the mid-point of the mass (M/Z) cluster.

Software used to analyze the data can include code that applies an algorithm to the analysis of the signal to determine whether the signal represents a peak in a signal that corresponds to a biomarker according to the present invention. The software also can subject the data regarding observed biomarker peaks to classification tree or ANN analysis, to determine whether a biomarker peak or combination of biomarker peaks is present that indicates the status of the particular clinical parameter under examination. Analysis of the data may be "keyed" to a variety of parameters that are obtained, either directly or indirectly, from the mass spectrometric analysis of the sample. These parameters include, but are not limited to, the presence or absence of one or more peaks, the shape of a peak or group of peaks, the height of one or more peaks, the log of the height of one or more peaks, and other arithmetic manipulations of peak height data.

General Protocol for SELDI Detection of Biomarkers for Prostate Cancer

A preferred protocol for the detection of the biomarker of this invention is as follows. The biological sample to be tested, e.g., urine, preferably is subject to pre-fractionation before SELDI analysis. This simplifies the sample and improves sensitivity. A preferred method of pre-fractionation involves contacting the sample with an anion exchange chromatographic material, such as Q HyperD (BioSepra, SA). The bound materials are then subject to stepwise pH elution using buffers at pH 9, pH 7, pH 5 and pH 4. (See Example 1—Buffer list.) (The fractions in which the biomarkers are eluted also is indicated in Table 1.) Various fractions containing the biomarker are collected.

The sample to be tested (preferably pre-fractionated) is then contacted with an affinity capture probe comprising an cation exchange adsorbent (preferably a WCX ProteinChip array (Ciphergen Biosystems, Inc.)) or an IMAC adsorbent (preferably an IMAC3 ProteinChip array (Ciphergen Biosystems, Inc.)), again as indicated in Table 1. The probe is washed with a buffer that will retain the biomarker while washing away unbound molecules. A suitable wash for each biomarker is the buffer identified in Table 1. The biomarkers are detected by laser desorption/ionization mass spectrometry.

Alternatively, if antibodies that recognize the biomarker are available, for example in the case of β2-microglobulin, cystatin, transferrin, transthyretin or albumin, these can be attached to the surface of a probe, such as a pre-activated PS10 or PS20 ProteinChip array (Ciphergen Biosystems, Inc.). These antibodies can capture the biomarkers from a sample onto the probe surface. Then the biomarkers can be detected by, e.g. laser desorption/ionization mass spectrometry.

4.2. Detection by Immunoassay

In another embodiment, the biomarker of this invention can be measured by immunoassay. Immunoassay requires biospecific capture reagents, such as antibodies, to capture the biomarkers. Antibodies can be produced by methods well known in the art, e.g., by immunizing animals with the biomarkers. Biomarkers can be isolated from samples based on their binding characteristics. Alternatively, if the amino acid sequence of a polypeptide biomarker is known, the polypeptide can be synthesized and used to generate antibodies by methods well known in the art.

This invention contemplates traditional immunoassays including, for example, sandwich immunoassays including ELISA or fluorescence-based immunoassays, as well as other enzyme immunoassays. Nephelometry is an assay done in liquid phase, in which antibodies are in solution. Binding of the antigen to the antibody results in changes in absorbance, which is measured. In the SELDI-based immunoassay, a biospecific capture reagent for the biomarker is attached to the surface of an MS probe, such as a pre-activated ProteinChip array. The biomarker is then specifically captured on the biochip through this reagent, and the captured biomarker is detected by mass spectrometry.

5. Determination of Subject Prostate Cancer Status 5.1. Single Markers

The biomarker of the invention can be used in diagnostic tests to assess Prostate Cancer status in a subject, e.g., to diagnose Prostate Cancer. The phrase "prostate Cancer status" includes any distinguishable manifestation of the disease, including non-disease. For example, disease status includes, without limitation, the presence or absence of disease (e.g., Prostate Cancer v. non-Prostate Cancer), the risk of developing disease, the stage of the disease, the progress of disease (e.g., progress of disease or remission of disease over time) and the effectiveness or response to treatment of disease. Based on this status, further procedures may be indicated, including additional diagnostic tests or therapeutic procedures or regimens.

The power of a diagnostic test to correctly predict status is commonly measured as the sensitivity of the assay, the specificity of the assay or the area under a receiver operated characteristic ("ROC") curve. Sensitivity is the percentage of true positives that are predicted by a test to be positive, while specificity is the percentage of true negatives that are predicted by a test to be negative. An ROC curve provides the sensitivity of a test as a function of 1-specificity. The greater the area under the ROC curve, the more powerful the predictive value of the test. Other useful measures of the utility of a test are positive predictive value and negative predictive value. Positive predictive value is the percentage of people who test positive that are actually positive. Negative predictive value is the percentage of people who test negative that are actually negative.

The biomarker of this invention shows a statistical difference in different Prostate Cancer statuses of at least $p \leq 0.05$, $p \leq 10^{-2}$, $p \leq 10^{-3}$, $p \leq 104$ or $p \leq 10^{-5}$. Diagnostic tests that use these biomarkers alone or in combination show a sensitivity and specificity of at least 75%, at least 80%, at least 85%, at least 90%, at least 95%, at least 98% and about 100%.

PCI is differentially present in Prostate Cancer, and, therefore, each is individually useful in aiding in the determination of Prostate Cancer status. The method involves, first, measuring the selected biomarker in a subject sample using the methods described herein, e.g., capture on a SELDI biochip followed by detection by mass spectrometry and, second, comparing the measurement with a diagnostic amount or cut-off that distinguishes a positive Prostate Cancer status from a negative Prostate Cancer status. The diagnostic amount represents a measured amount of a biomarker above which or below which a subject is classified as having a particular Prostate Cancer status. For example, if the biomarker is up-regulated compared to normal during Prostate Cancer, then a measured amount above the diagnostic cutoff provides a diagnosis of Prostate Cancer. Alternatively, if the biomarker is down-regulated during Prostate Cancer, then a measured amount below the diagnostic cutoff provides a diagnosis of Prostate Cancer. As is well understood in the art, by adjusting the particular diagnostic cut-off used in an assay, one can increase sensitivity or specificity of the diagnostic assay depending on the preference of the diagnostician. The particular diagnostic cut-off can be determined, for example, by measuring the amount of the biomarker in a statistically significant number of samples from subjects with the different Prostate Cancer statuses, as was done here, and drawing the cut-off to suit the diagnostician's desired levels of specificity and sensitivity.

5.2. Determining Risk of Developing Disease

In one embodiment, this invention provides methods for determining the risk of developing disease in a subject. Biomarker amounts or patterns are characteristic of various risk states, e.g., high, medium or low. The risk of developing a disease is determined by measuring the relevant biomarker or biomarkers and then either submitting them to a classification algorithm or comparing them with a reference amount and/or pattern of biomarkers that is associated with the particular risk level.

5.3. Determining Stage of Disease

In one embodiment, this invention provides methods for determining the stage of disease in a subject. Each stage of the disease has a characteristic amount of a biomarker or relative amounts of a set of biomarkers (a pattern). The stage of a disease is determined by measuring the relevant biomarker or biomarkers and then either submitting them to a classification algorithm or comparing them with a reference amount and/or pattern of biomarkers that is associated with the particular stage.

5.4 Determining Course (Progression/Remission) of Disease

In one embodiment, this invention provides methods for determining the course of disease in a subject. Disease course refers to changes in disease status over time, including disease progression (worsening) and disease regression (improvement). Over time, the amounts or relative amounts (e.g., the pattern) of the biomarkers changes. For example, biomarker PCI is increased with disease, while biomarker "Z" is decreased in disease. Therefore, the trend of these markers, either increased or decreased over time toward diseased or non-diseased indicates the course of the disease. Accordingly, this method involves measuring one or more biomarkers in a subject at least two different time points, e.g., a first time and a second time, and comparing the change in amounts, if any. The course of disease is determined based on these comparisons.

5.5. Subject Management

In certain embodiments of the methods of qualifying Prostate Cancer status, the methods further comprise managing subject treatment based on the status. Such management includes the actions of the physician or clinician subsequent to determining Prostate Cancer status. For example, if a physician makes a diagnosis of Prostate Cancer, then a certain regime of treatment, such as prescription or administration of therapeutic agent might follow. Alternatively, a diagnosis of non-Prostate Cancer or non-Prostate Cancer might be followed with further testing to determine a specific disease that might the patient might be suffering from. Also, if the diagnostic test gives an inconclusive result on Prostate Cancer status, further tests may be called for.

Additional embodiments of the invention relate to the communication of assay results or diagnoses or both to technicians, physicians or patients, for example. In certain embodiments, computers will be used to communicate assay results or diagnoses or both to interested parties, e.g., physicians and their patients. In some embodiments, the assays will be performed or the assay results analyzed in a country or jurisdiction which differs from the country or jurisdiction to which the results or diagnoses are communicated.

In a preferred embodiment of the invention, a diagnosis based on the presence or absence in a test subject of the biomarker is communicated to the subject as soon as possible after the diagnosis is obtained. The diagnosis may be communicated to the subject by the subject's treating physician. Alternatively, the diagnosis may be sent to a test subject by email or communicated to the subject by phone. A computer may be used to communicate the diagnosis by email or phone. In certain embodiments, the message containing results of a diagnostic test may be generated and delivered automatically to the subject using a combination of computer hardware and software which will be familiar to artisans skilled in telecommunications. One example of a healthcare-oriented communications system is described in U.S. Pat. No. 6,283,761; however, the present invention is not limited to methods which utilize this particular communications system. In certain embodiments of the methods of the invention, all or some of the method steps, including the assaying of samples, diagnosing of diseases, and communicating of assay results or diagnoses, may be carried out in diverse (e.g., foreign) jurisdictions.

5.6 Determining Therapeutic Efficacy of Pharmaceutical Drug

In another embodiment, this invention provides methods for determining the therapeutic efficacy of a pharmaceutical drug. These methods are useful in performing clinical trials of the drug, as well as monitoring the progress of a patient on the drug. Therapy or clinical trials involve administering the drug in a particular regimen. The regimen may involve a single dose of the drug or multiple doses of the drug over time. The doctor or clinical researcher monitors the effect of the drug on the patient or subject over the course of administration. If the drug has a pharmacological impact on the condition, the amounts or relative amounts (e.g., the pattern or profile) of the biomarkers of this invention changes toward a non-disease profile. Therefore, one can follow the course of the amounts of these biomarkers in the subject during the course of treatment. Accordingly, this method involves measuring one or more biomarkers in a subject receiving drug therapy, and correlating the amounts of the biomarkers with the disease status of the subject. One embodiment of this method involves determining the levels of the biomarkers at least two different time points during a course of drug therapy, e.g., a first time and a second time, and comparing the change in amounts of the biomarkers, if any. For example, the biomarkers can be measured before and after drug administration or at two different time points during drug administration. The effect of therapy is determined based on these comparisons. If a treatment is effective, then the biomarkers will trend toward normal, while if treatment is ineffective, the biomarkers will trend toward disease indications. If a treatment is effective, then the biomarkers will trend toward normal, while if treatment is ineffective, the biomarkers will trend toward disease indications.

6. Generation of Classification Algorithms for Qualifying Prostate Cancer Status In some embodiments, data derived from the spectra (e.g., mass spectra or time-of-flight spectra) that are generated using samples such as "known samples" can then be used to "train" a classification model. A "known sample" is a sample that has been pre-classified. The data that are derived from the spectra and are used to form the classification model can be referred to as a "training data set." Once trained, the classification model can recognize patterns in data derived from spectra generated using unknown samples. The classification model can then be used to classify the unknown samples into classes. This can be useful, for example, in predicting whether or not a particular biological sample is associated with a certain biological condition (e.g., diseased versus non-diseased).

The training data set that is used to form the classification model may comprise raw data or pre-processed data. In some embodiments, raw data can be obtained directly from time-of-flight spectra or mass spectra, and then may be optionally "pre-processed" as described above.

Classification models can be formed using any suitable statistical classification (or "learning") method that attempts to segregate bodies of data into classes based on objective parameters present in the data. Classification methods may be either supervised or unsupervised. Examples of supervised and unsupervised classification processes are described in Jain, "Statistical Pattern Recognition: A Review", *IEEE Transactions on Pattern Analysis and Machine Intelligence*, Vol. 22, No. 1, January 2000, the teachings of which are incorporated by reference.

In supervised classification, training data containing examples of known categories are presented to a learning mechanism, which learns one or more sets of relationships that define each of the known classes. New data may then be applied to the learning mechanism, which then classifies the new data using the learned relationships. Examples of supervised classification processes include linear regression processes (e.g. multiple linear regression (MLR), partial least squares (PLS) regression and principal components regression (PCR)), binary decision trees (e.g., recursive partitioning processes such as CART—classification and regression trees), artificial neural networks such as back propagation networks, discriminant analyses (e.g., Bayesian classifier or Fischer analysis), logistic classifiers, and support vector classifiers (support vector machines).

A preferred supervised classification method is a recursive partitioning process. Recursive partitioning processes use recursive partitioning trees to classify spectra derived from unknown samples. Further details about recursive partitioning processes are provided in U.S. Patent Application No. 2002 0138208 A1 to Paulse et al., "Method for analyzing mass spectra."

In other embodiments, the classification models that are created can be formed using unsupervised learning methods. Unsupervised classification attempts to learn classifications based on similarities in the training data set, without pre-classifying the spectra from which the training data set was derived. Unsupervised learning methods include cluster analyses. A cluster analysis attempts to divide the data into "clusters" or groups that ideally should have members that are very similar to each other, and very dissimilar to members of other clusters. Similarity is then measured using some distance metric, which measures the distance between data items, and clusters together data items that are closer to each other. Clustering techniques include the MacQueen's K-means algorithm and the Kohonen's Self-Organizing Map algorithm.

Learning algorithms asserted for use in classifying biological information are described, for example, in PCT International Publication No. WO 01/31580 (Barnhill et al., "Methods and devices for identifying patterns in biological systems and methods of use thereof"), U.S. Patent Application No. 2002 0193950 A1 (Gavin et al. "Method or analyzing mass spectra"), U.S. Patent Application No. 2003 0004402 A1 (Hitt et al., "Process for discriminating between biological states based on hidden patterns from biological data"), and U.S. Patent Application No. 2003 0055615 A1 (Zhang and Zhang, "Systems and methods for processing biological expression data").

The classification models can be formed on and used on any suitable digital computer. Suitable digital computers include micro, mini, or large computers using any standard or specialized operating system, such as a Unix, Windows™ or Linux™ based operating system. The digital computer that is used may be physically separate from the mass spectrometer that is used to create the spectra of interest, or it may be coupled to the mass spectrometer.

The training data set and the classification models according to embodiments of the invention can be embodied by computer code that is executed or used by a digital computer. The computer code can be stored on any suitable computer readable media including optical or magnetic disks, sticks, tapes, etc., and can be written in any suitable computer programming language including C, C++, visual basic, etc.

The learning algorithms described above are useful both for developing classification algorithms for the biomarkers already discovered, or for finding new biomarkers for Prostate Cancer. The classification algorithms, in turn, form the base for diagnostic tests by providing diagnostic values (e.g., cut-off points) for biomarkers used singly or in combination.

7. Compositions of Matter

In another aspect, this invention provides compositions of matter based on the biomarker of this invention.

In one embodiment, this invention provides a biomarker of this invention in purified form. Purified biomarkers have utility as antigens to raise antibodies. Purified biomarkers also have utility as standards in assay procedures. As used herein, a "purified biomarker" is a biomarker that has been isolated from other proteins and peptides, and/or other material from the biological sample in which the biomarker is found. Biomarkers may be purified using any method known in the art, including, but not limited to, mechanical separation (e.g., centrifugation), ammonium sulphate precipitation, dialysis (including size-exclusion dialysis), size-exclusion chromatography, affinity chromatography, anion-exchange chromatography, cation-exchange chromatography, and methal-chelate chromatography. Such methods may be performed at any appropriate scale, for example, in a chromatography column, or on a biochip.

In another embodiment, this invention provides a biospecific capture reagent, optionally in purified form, that specifically binds a biomarker of this invention. In one embodiment, the biospecific capture reagent is an antibody. Such compositions are useful for detecting the biomarker in a detection assay, e.g., for diagnostics.

In another embodiment, this invention provides an article comprising a biospecific capture reagent that binds a biomarker of this invention, wherein the reagent is bound to a solid phase. For example, this invention contemplates a device comprising bead, chip, membrane, monolith or microtiter plate derivatized with the biospecific capture reagent. Such articles are useful in biomarker detection assays.

In another aspect this invention provides a composition comprising a biospecific capture reagent, such as an antibody, bound to a biomarker of this invention, the composition optionally being in purified form. Such compositions are useful for purifying the biomarker or in assays for detecting the biomarker.

In another embodiment, this invention provides an article comprising a solid substrate to which is attached an adsorbent, e.g., a chromatographic adsorbent or a biospecific capture reagent, to which is further bound a biomarker of this invention. In one embodiment, the article is a biochip or a probe for mass spectrometry, e.g., a SELDI probe. Such articles are useful for purifying the biomarker or detecting the biomarker.

8. Kits for Detection of Biomarkers for Prostate Cancer

In another aspect, the present invention provides kits for qualifying Prostate Cancer status, which kits are used to detect the biomarker according to the invention. In one embodiment, the kit comprises a solid support, such as a chip, a microtiter plate or a bead or resin having a capture reagent attached thereon, wherein the capture reagent binds a biomarker of the invention. Thus, for example, the kits of the present invention can comprise mass spectrometry probes for SELDI, such as ProteinChip® arrays. In the case of biospecfic capture reagents, the kit can comprise a solid support with a reactive surface, and a container comprising the biospecific capture reagent.

The kit can also comprise a washing solution or instructions for making a washing solution, in which the combination of the capture reagent and the washing solution allows capture of the biomarker or biomarkers on the solid support for subsequent detection by, e.g., mass spectrometry. The kit may include more than type of adsorbent, each present on a different solid support.

In a further embodiment, such a kit can comprise instructions for suitable operational parameters in the form of a label or separate insert. For example, the instructions may inform a consumer about how to collect the sample, how to wash the probe or the particular biomarkers to be detected.

In yet another embodiment, the kit can comprise one or more containers with biomarker samples, to be used as standard(s) for calibration.

9. Use of Biomarkers for Prostate Cancer in Screening Assays and Methods of Treating Prostate Cancer The methods of the present invention have other applications as well. For example, the biomarker can be used to screen for compounds that modulate the expression of the biomarker in vitro or in vivo, which compounds in turn may be useful in treating or preventing Prostate Cancer in patients. In another example, the biomarkers can be used to monitor the response to treatments for Prostate Cancer. In yet another example, the biomarkers can be used in heredity studies to determine if the subject is at risk for developing Prostate Cancer.

Thus, for example, the kits of this invention could include a solid substrate having a hydrophobic function, such as a protein biochip (e.g., a Ciphergen H50 ProteinChip array, e.g., ProteinChip array) and a sodium acetate buffer for washing the substrate, as well as instructions providing a protocol to measure the biomarkers of this invention on the chip and to use these measurements to diagnose Prostate Cancer.

Compounds suitable for therapeutic testing may be screened initially by identifying compounds which interact with one or more biomarkers listed in Table I. By way of example, screening might include recombinantly expressing the biomarker listed in Table I, purifying the biomarker, and affixing the biomarker to a substrate. Test compounds would then be contacted with the substrate, typically in aqueous conditions, and interactions between the test compound and the biomarker are measured, for example, by measuring elution rates as a function of salt concentration. Certain proteins may recognize and cleave the biomarkers of Table I, in which case the proteins may be detected by monitoring the digestion of one or more biomarkers in a standard assay, e.g., by gel electrophoresis of the proteins.

In a related embodiment, the ability of a test compound to inhibit the activity of the of the biomarker of Table I may be measured. One of skill in the art will recognize that the techniques used to measure the activity of a particular biomarker will vary depending on the function and properties of the biomarker. For example, an enzymatic activity of a biomarker may be assayed provided that an appropriate substrate is available and provided that the concentration of the substrate or the appearance of the reaction product is readily measurable. The ability of potentially therapeutic test compounds to inhibit or enhance the activity of a given biomarker may be determined by measuring the rates of catalysis in the presence or absence of the test compounds. The ability of a test compound to interfere with a non-enzymatic (e.g., structural) function or activity of one of the biomarkers of Table I may also be measured. For example, the self-assembly of a multi-protein complex which includes one of the biomarkers of Table I may be monitored by spectroscopy in the presence or absence of a test compound. Alternatively, if the biomarker is a non-enzymatic enhancer of transcription, test compounds which interfere with the ability of the biomarker to enhance transcription may be identified by measuring the levels of biomarker-dependent transcription in vivo or in vitro in the presence and absence of the test compound.

Test compounds capable of modulating the activity of the biomarker of Table I may be administered to patients who are suffering from or are at risk of developing Prostate Cancer or other cancer. For example, the administration of a test compound which increases the activity of a particular biomarker may decrease the risk of Prostate Cancer in a patient if the activity of the particular biomarker in vivo prevents the accumulation of proteins for Prostate Cancer. Conversely, the administration of a test compound which decreases the activity of a particular biomarker may decrease the risk of Prostate Cancer in a patient if the increased activity of the biomarker is responsible, at least in part, for the onset of Prostate Cancer.

In an additional aspect, the invention provides a method for identifying compounds useful for the treatment of disorders such as Prostate Cancer which are associated with increased levels of modified forms of PCI. For example, in one embodiment, cell extracts or expression libraries may be screened for compounds which catalyze the cleavage of full-length PCI to form truncated forms of PCI. In one embodiment of such a screening assay, cleavage of PCI may be detected by attaching a fluorophore to PCI which remains quenched when PCI is uncleaved but which fluoresces when the protein is cleaved. Alternatively, a version of full-length PCI modified so as to render the amide bond between amino acids x and y uncleavable may be used to selectively bind or "trap" the cellular protesase which cleaves full-length PCI at that site in vivo. Methods for screening and identifying proteases and their targets are well-documented in the scientific literature, e.g., in Lopez-Ottin et al. (Nature Reviews, 3:509-519 (2002)).

In yet another embodiment, the invention provides a method for treating or reducing the progression or likelihood of a disease, e.g., Prostate Cancer, which is associated with the increased levels of truncated PCI. For example, after one or more proteins have been identified which cleave full-length PCI, combinatorial libraries may be screened for compounds which inhibit the cleavage activity of the identified proteins. Methods of screening chemical libraries for such compounds are well-known in art. See, e.g., Lopez-Otin et al. (2002). Alternatively, inhibitory compounds may be intelligently designed based on the structure of PCI.

N-terminal truncations of PCI are thought to diminish PCI's protease inhibitory activity. See, e.g., Abrahamson et al. (Biochem. J. 273:621-626 (1991)). Compounds which impart truncated PCI with the functionality of full-length PCI are likely therefore to be useful in treating conditions, such as Prostate Cancer, which are associated with the truncated form of PCI. Therefore, in a further embodiment, the invention provides methods for identifying compounds which increase the affinity of truncated PCI for its target proteases. For example, compounds may be screened for their ability to impart truncated PCI with the protease inhibitory activity of full-length PCI. Test compounds capable of modulating the inhibitory activity of PCI or the activity of molecules which interact with PCI may then be tested in vivo for their ability to slow or stop the progression of Prostate Cancer in a subject.

At the clinical level, screening a test compound includes obtaining samples from test subjects before and after the subjects have been exposed to a test compound. The levels in the samples of the biomarker listed in Table I may be measured and analyzed to determine whether the levels of the biomarkers change after exposure to a test compound. The samples may be analyzed by mass spectrometry, as described herein, or the samples may be analyzed by any appropriate means known to one of skill in the art. For example, the levels of the biomarkers listed in Table I may be measured directly by Western blot using radio- or fluorescently-labeled antibodies which specifically bind to the biomarkers. Alternatively, changes in the levels of mRNA encoding the one or more biomarkers may be measured and correlated with the administration of a given test compound to a subject. In a further embodiment, the changes in the level of expression of one or more of the biomarkers may be measured using in vitro methods and materials. For example, human tissue cultured cells which express, or are capable of expressing, one or more of the biomarkers of Table I may be contacted with test compounds. Subjects who have been treated with test compounds will be routinely examined for any physiological effects which may result from the treatment. In particular, the test compounds will be evaluated for their ability to decrease disease likelihood in a subject. Alternatively, if the test compounds are administered to subjects who have previously been diagnosed with Prostate Cancer, test compounds will be screened for their ability to slow or stop the progression of the disease.

10. Examples 10.1. Example 1

Discovery of a Biomarker for Prostate Cancer

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

Example 1

Identification of Protein C Inhibitor

The 3890 Da protein was detected in Q fraction 6 using CM10 arrays. Provided representative profiling spectra were internally recalibrated using known identified proteins. The average MW (from seven spectra) of the targeted protein was calculated to be 3890.23 Da (FIG. 1).

Figure 2:
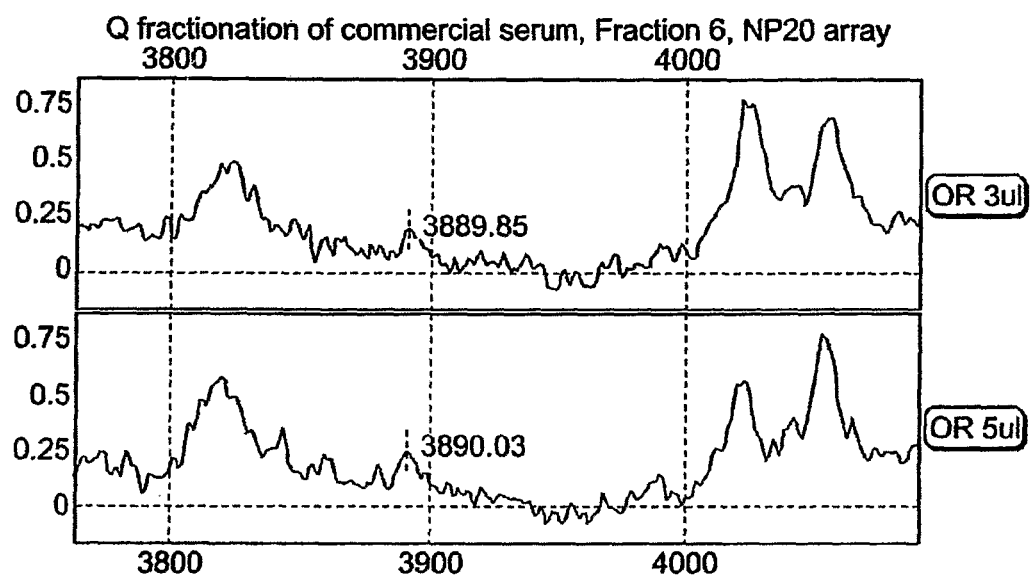
FIG. 2 shows representative profiling mass spectra for the PCI biomarker of commercial serum. In those Figures, the mass spectral peak of the specified marker is designated within the depicted spectra with the molecular weight.
Figure 3:
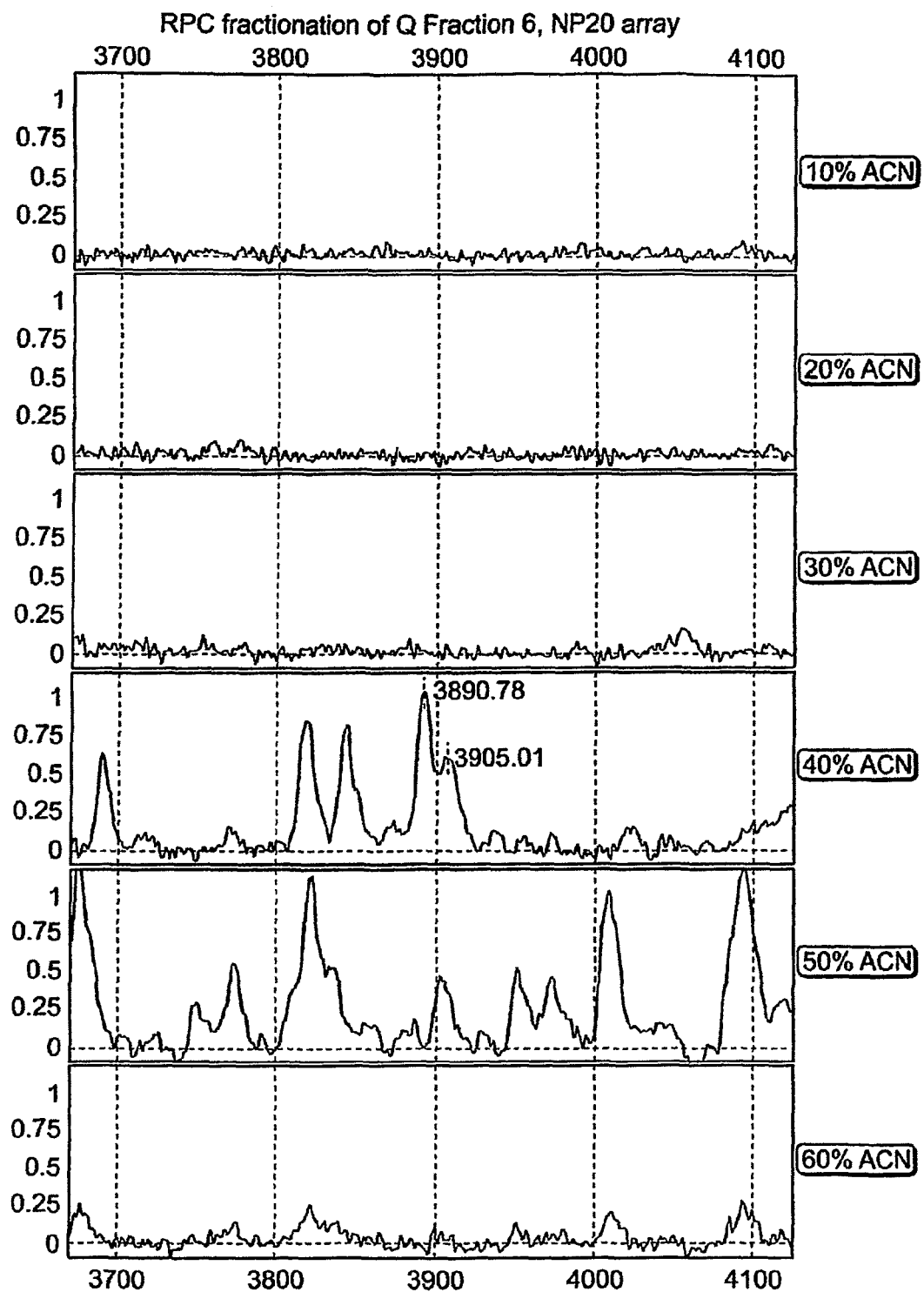
FIG. 3 shows representative profiling spectra using RPC fractionation of Q Fraction 6. In those Figures, the mass spectral peak of the specified marker is designated within the depicted spectra with the molecular weight.

The 3890 Da protein is present in the commercial pooled serum (FIG. 1, spectrum "C"). Importantly, in contrast to clinical samples the commercial serum is almost void of Platelet Factor 4, whose 2+ ion quite precisely overlaps with the ion of the 3890 Da protein. 1 ml of commercial serum was fractionated under denaturing conditions using anion exchange chromatography (Q HyperD F). Profiling of the organic fraction using NP20 array confirmed a presence of the 3890 Da peak (FIG. 2). Fraction 6 was further fractionated using reverse phase chromatography. The 3890 Da protein was eluted from RPC beads with 40% ACN (FIG. 3). Absence of PF4 in the resulting preparation confirms that the 3890 Da peak is bona fide protein and is not 2+ ion (though we can not rule out that the 2+ ion of PF4 may contribute to the intensity of the 3890 Da peak in the profiling study).

Figure 4:
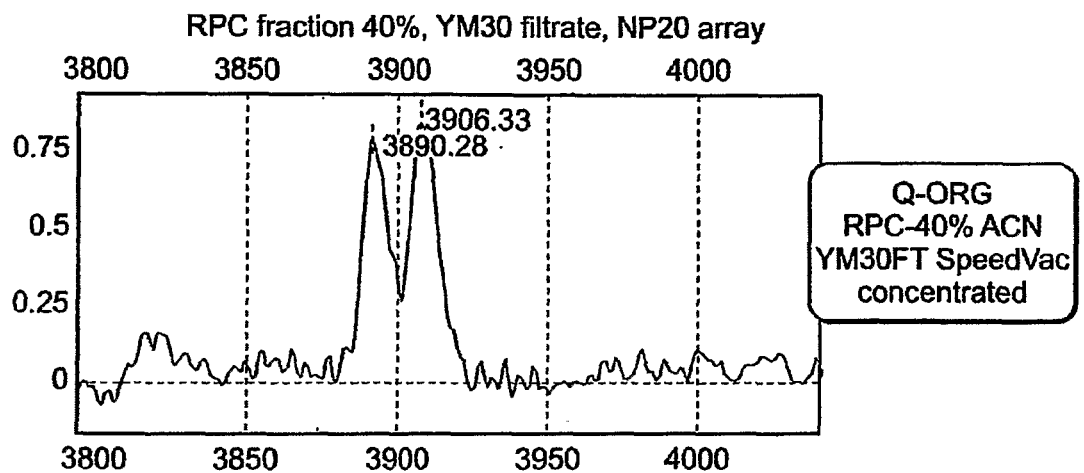
FIG. 4 shows a representative profiling spectra using RPC fraction 40%, YM30 filtrate and NP20 array. In those Figures, the mass spectral peak of the specified marker is designated within the depicted spectra with the molecular weight.

Methionine is stable at neutral alkaline pH. However, it undergoes a significant oxidation at acidic pH (CM10 and H50 array profiling, reverse phase chromatography, cut-off membrane fractionation in the presence of ACN and TFA, etc.). It was observed that the 3890 Da protein from Q fraction 6 was gradually oxidized during enrichment (FIGS. 3 and 4), indicating that the candidate biomarker contains one Methionine.

Neither SDS-PAGE purification nor direct sequencing of the Q-Fr.6 3890 Da peak is feasible for amounts enriched from 1 ml of serum (FIG. 3). My lowest estimate for starting material is 20 ml of reference serum or clinical sample.

Figure 5:
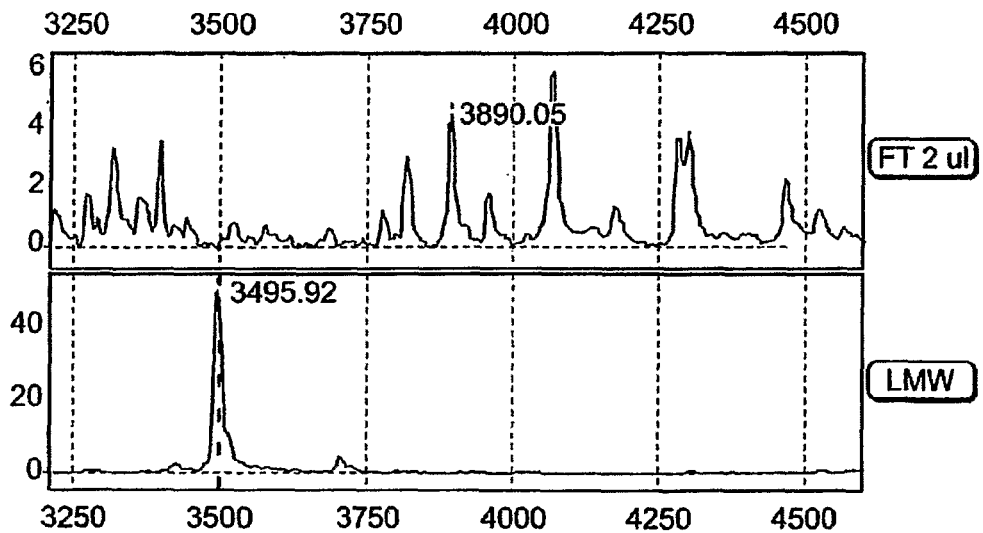
FIG. 5 shows representative profiling mass spectra using Q fractionation of commercial serum and CM10 array. In those Figures, the mass spectral peak of the specified marker is designated within the depicted spectra with the molecular weight.
Figure 6:
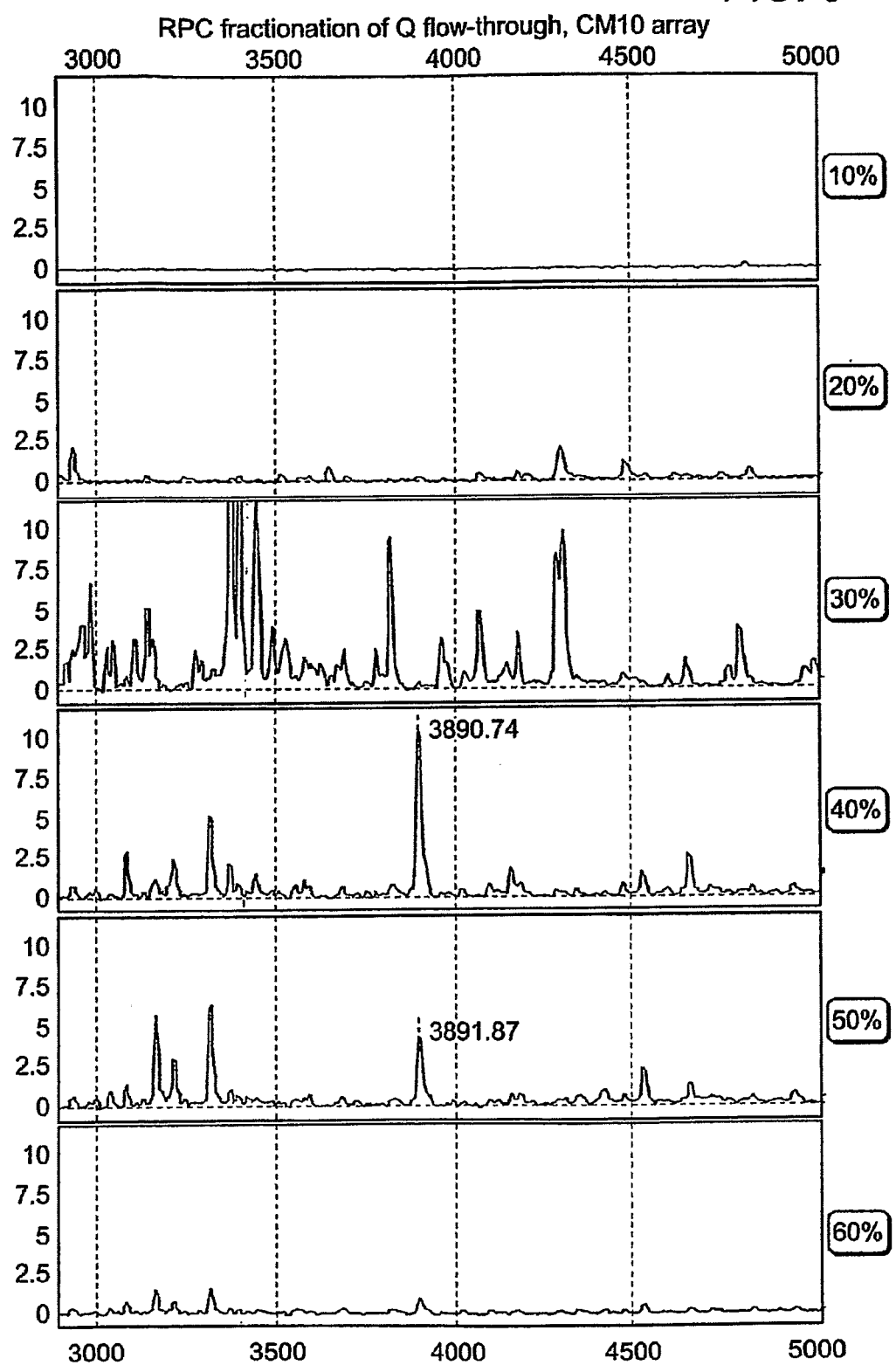
FIG. 6 shows representative profiling mass spectra using RPC fractionation of Q flow-through and CM10 array. In those Figures, the mass spectral peak of the specified marker is designated within the depicted spectra with the molecular weight.
Figure 7:
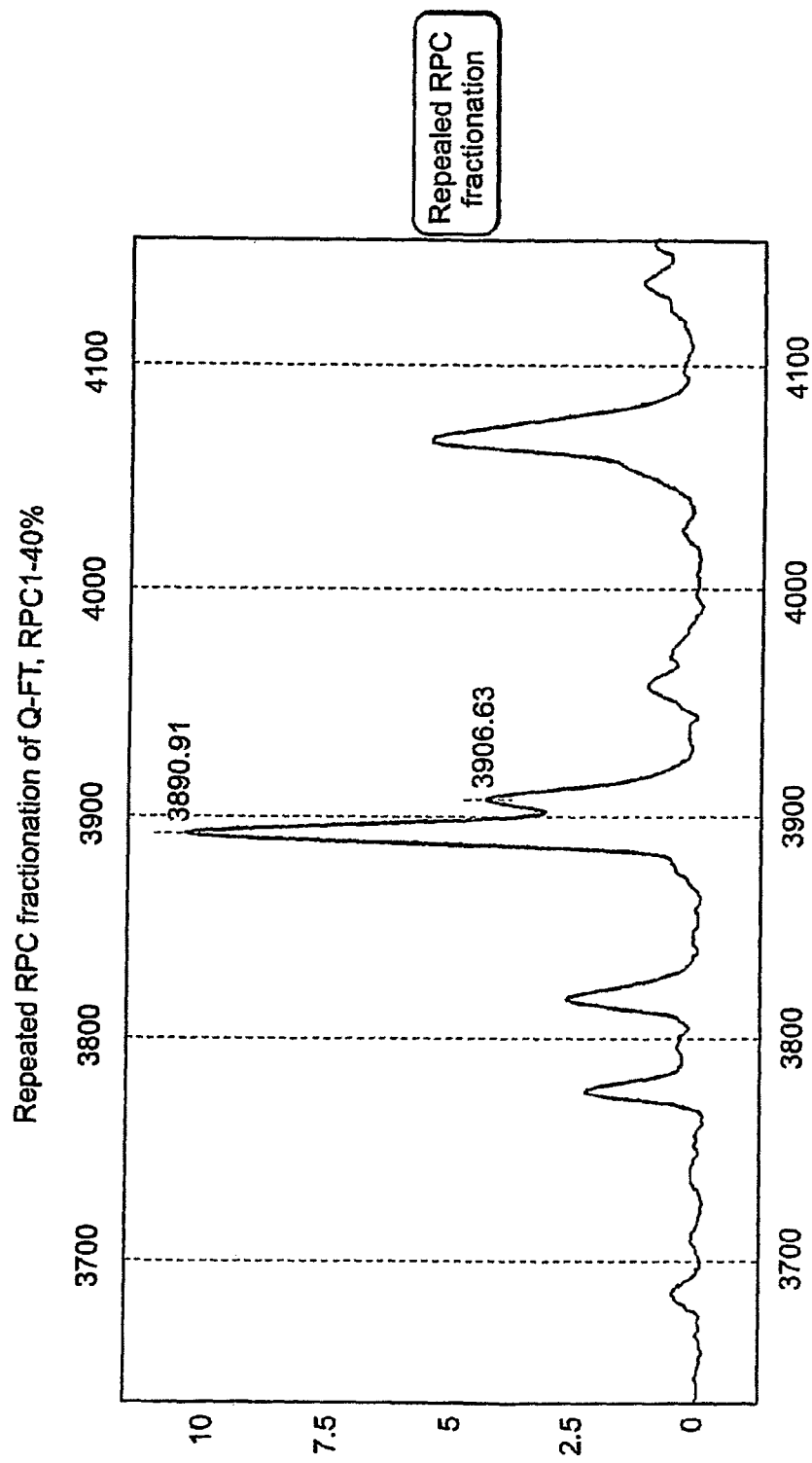
FIG. 7 shows a representative profiling mass spectra using repeated RPC fractionation of Q-FT, RPC1-40%. In those Figures, the mass spectral peak of the specified marker is designated within the depicted spectra with the molecular weight.

No protein can remain specifically bound to an anion exchange resin below pH 3 (the most acidic hypothetical proteins EEEEEEEEEE (SEQ ID NO: 11) and DDDDDDDD (SEQ ID NO: 12) have pI 3.47 and 3.08, respectively). A common observation from past projects is that any protein detected in Fraction 6 can be also found (and in most cases in much higher amounts) in other Q fraction matching the protein's pI. Therefore Q fractions were profiled using CM10 arrays. Indeed, the 3890 Da peak can be clearly detected in the Q-Flow-through (FIG. 5). It elutes from RPC beads with 40% ACN very similarly to the Q-Fr.6 "sibling" (FIG. 6). The Q-FT 3890 Da protein like the Q-Fr.6 3890 Da protein was gradually oxidized during purification indicating that it contains one Methionine (FIG. 7).

Figure 8:
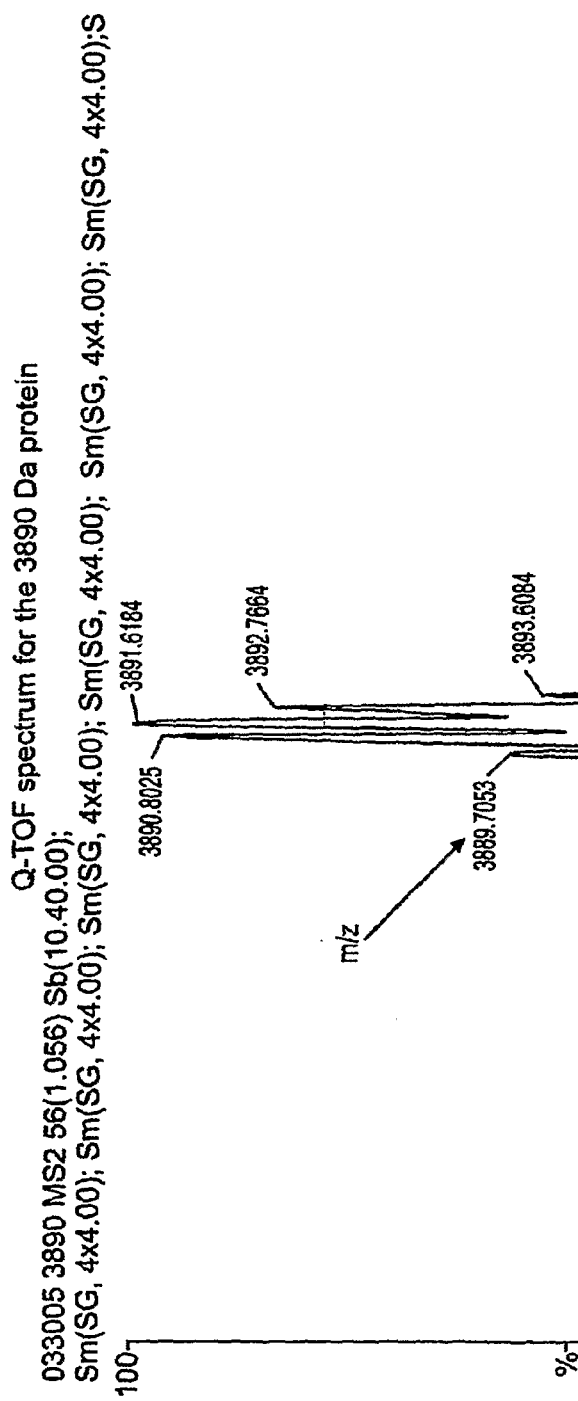
FIG. 8 shows representative profiling Q-TOFspectra for 3890 Da protein. In those Figures, the mass spectral peak of the specified marker is designated within the depicted spectra with the molecular weight.
Figure 9:
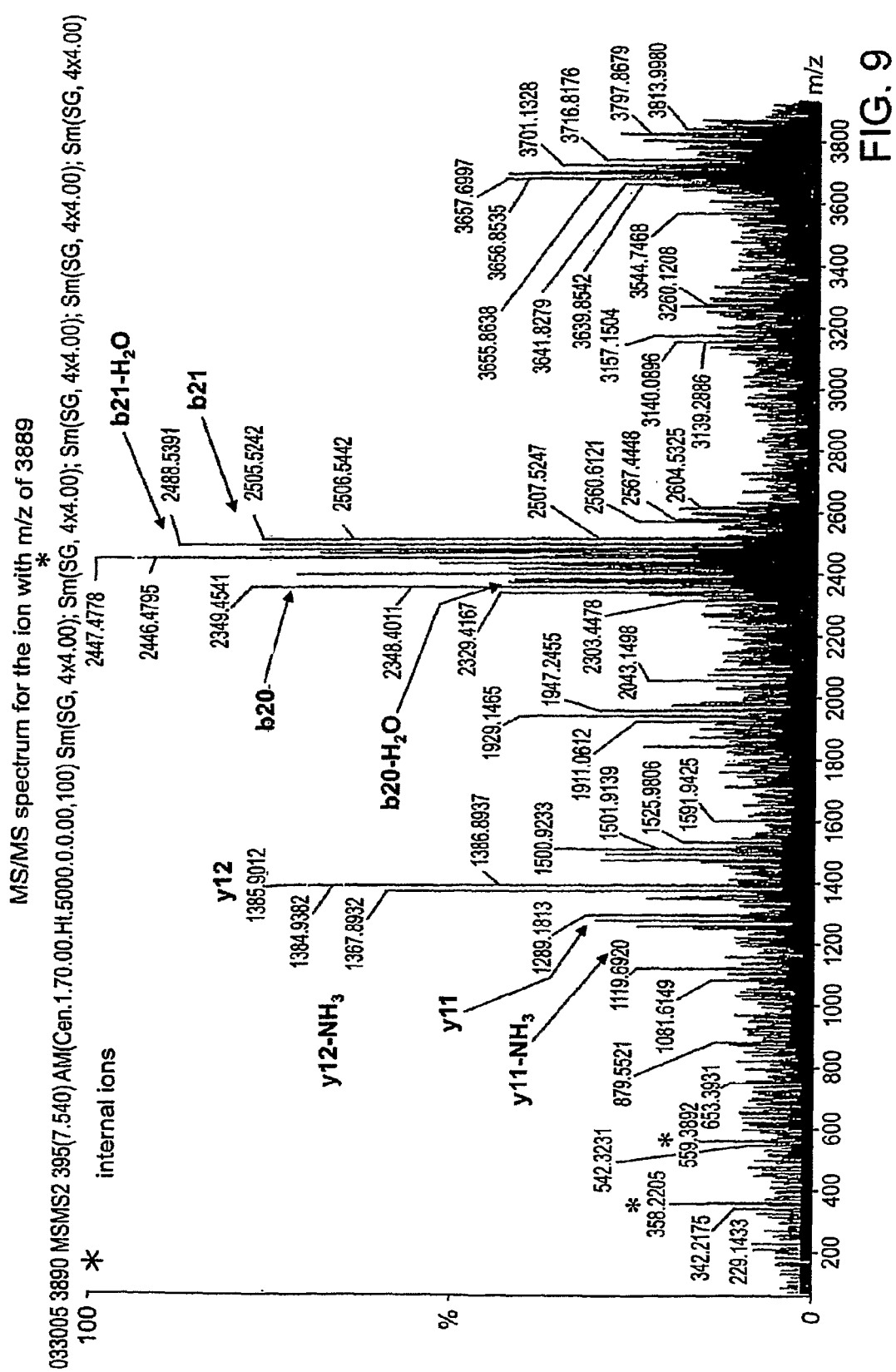
FIG. 9 shows representative profiling of MS/MS spectra for the ion with m/z of 3889. In those Figures, the mass spectral peak of the specified marker is designated within the depicted spectra with the molecular weight.
Figure 12:
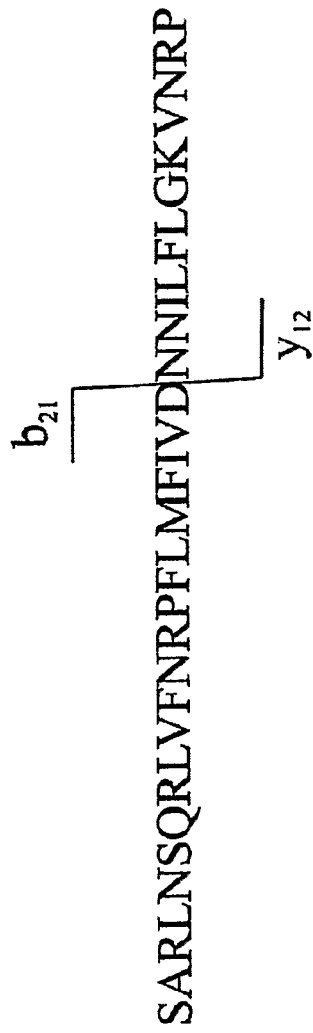
FIG. 12 is a representative interpretation of MS/MS data.

The 3890 Da protein was directly analyzed by Q-TOF MSMS (FIGS. 8, 9). Direct database search using Mascot search engine was not successful, therefore the MSMS data were interpreted manually using Protein Prospector tool. Unbiased search using the most intense ions resulted in too many candidates. However, one particular candidate, the naturally occurring C-terminal peptide of Plasma Protein C Inhibitor fitted best "manual" filtering criteria such as (1) physiological relevance, (2) number of Met, (3) any sense for a peptide to be generated in vivo, (4) explanation for m/z value errors for individual ions, (5) interpretation of ions based on predicted sites prone to fragmentation, (6) pairing of b- and y-ions, etc (FIGS. 9-14).

Figure 15:
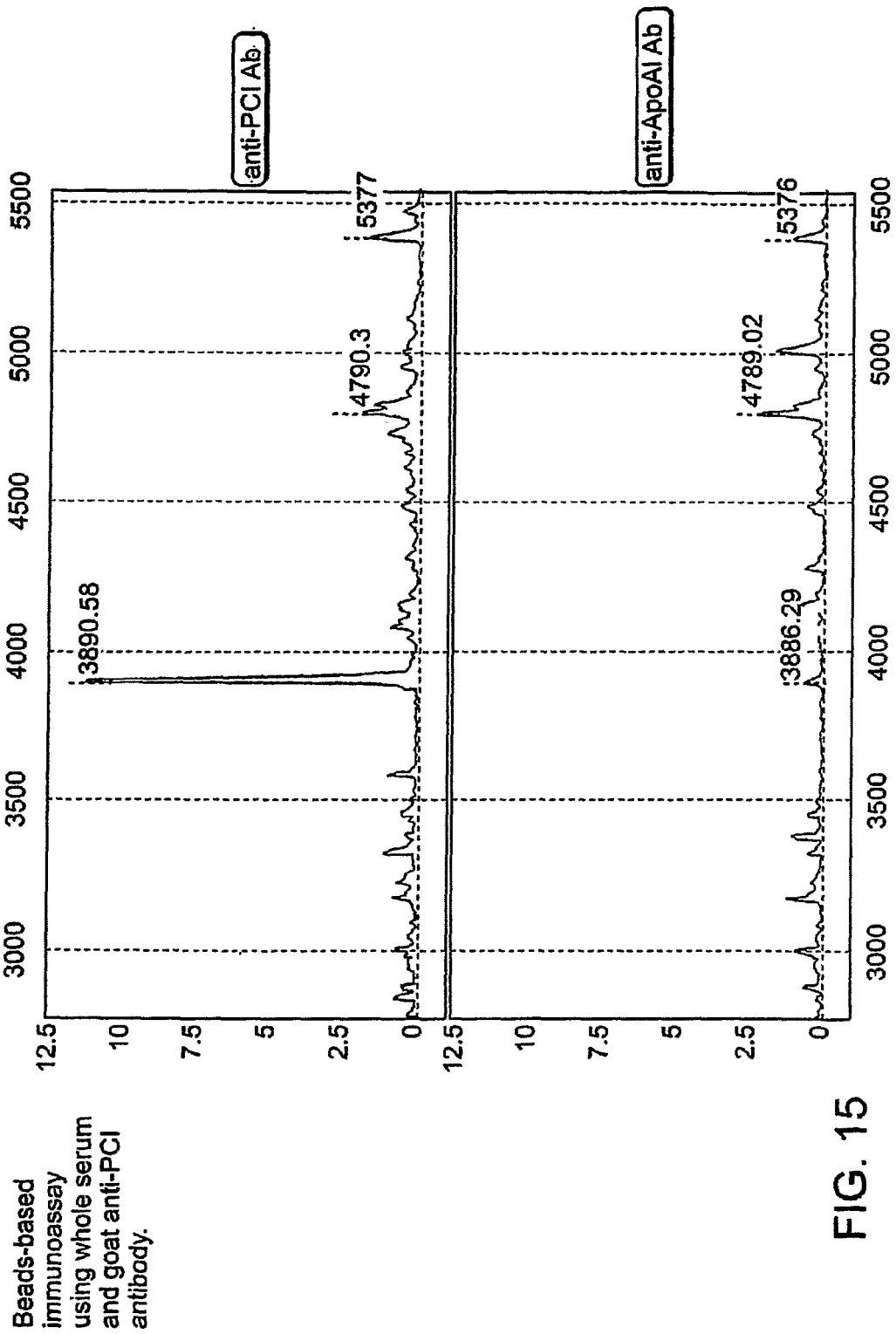
FIG. 15 is an illustration of the results of a bead-based immunoassay using whole serum and goat anti-PCI antibody.
Figure 16:
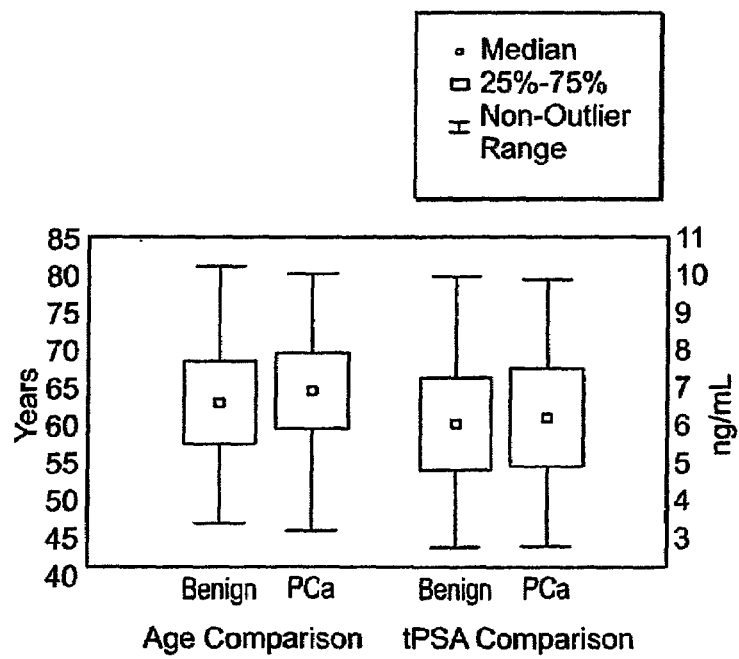
FIG. 16 represents data from Multicenter Sample Sets for Discovery and Validation.
Figure 17:
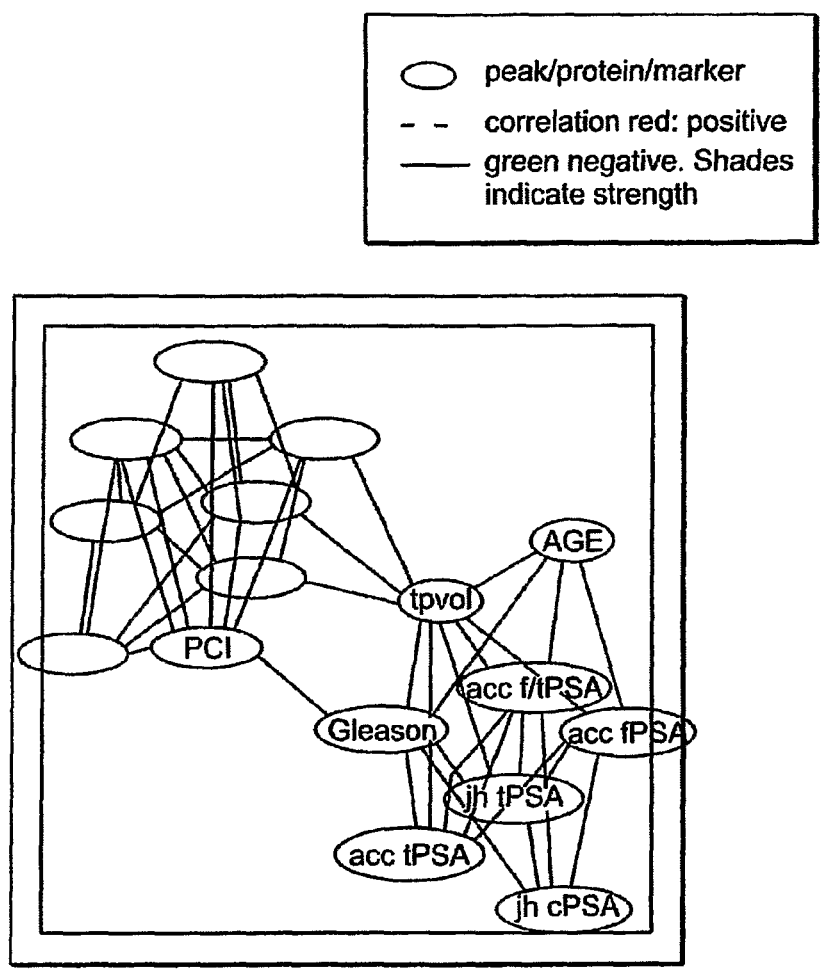
FIG. 17 is an illustration of Discovery through Correlation Network Analysis.
Figure 18:
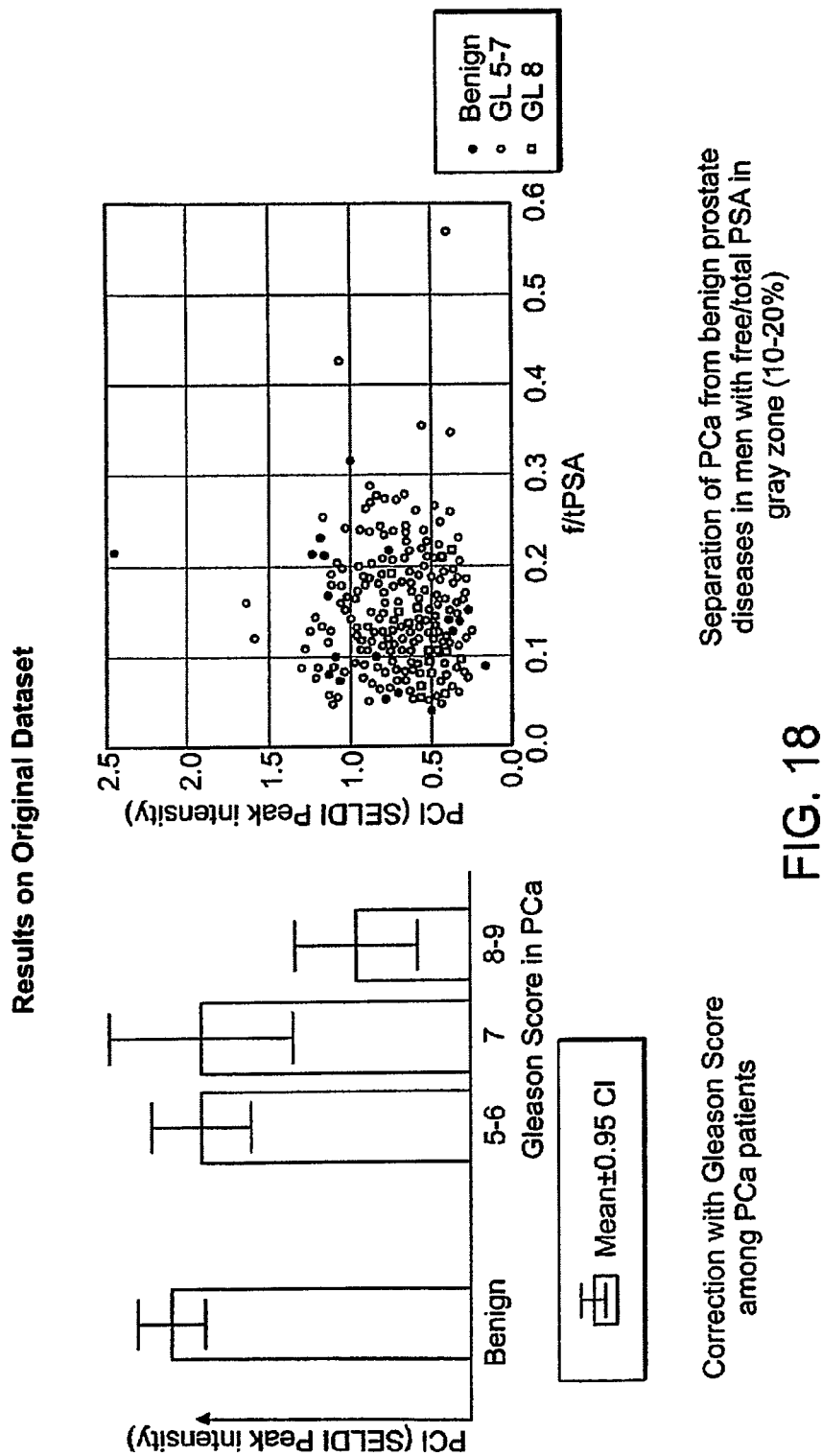
FIG. 18 are illustrations of data correlation with the Gleason Score and separation of prostate cancer from benign prostate diseases.
Figure 19:
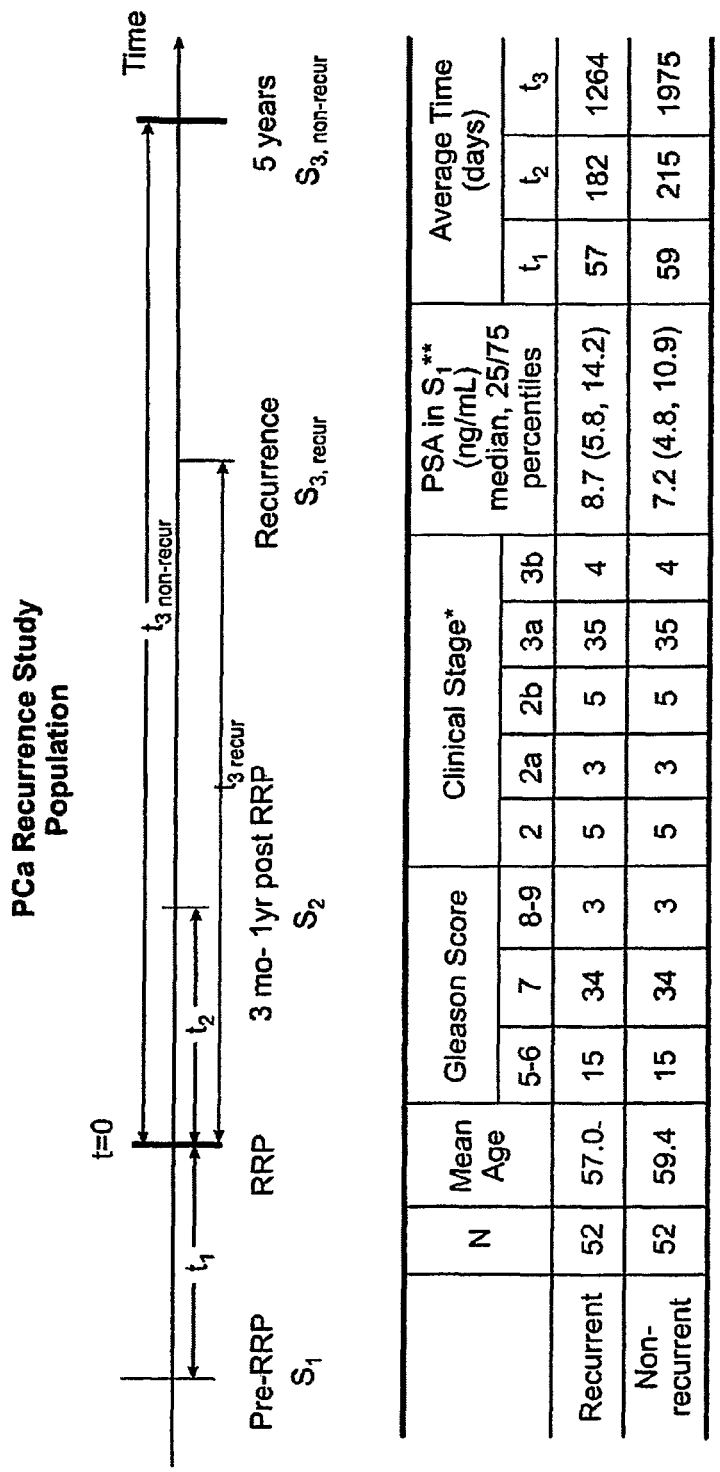
FIG. 19 is an illustration of the data correlation with recurrence of prostate cancer.
Figure 20:
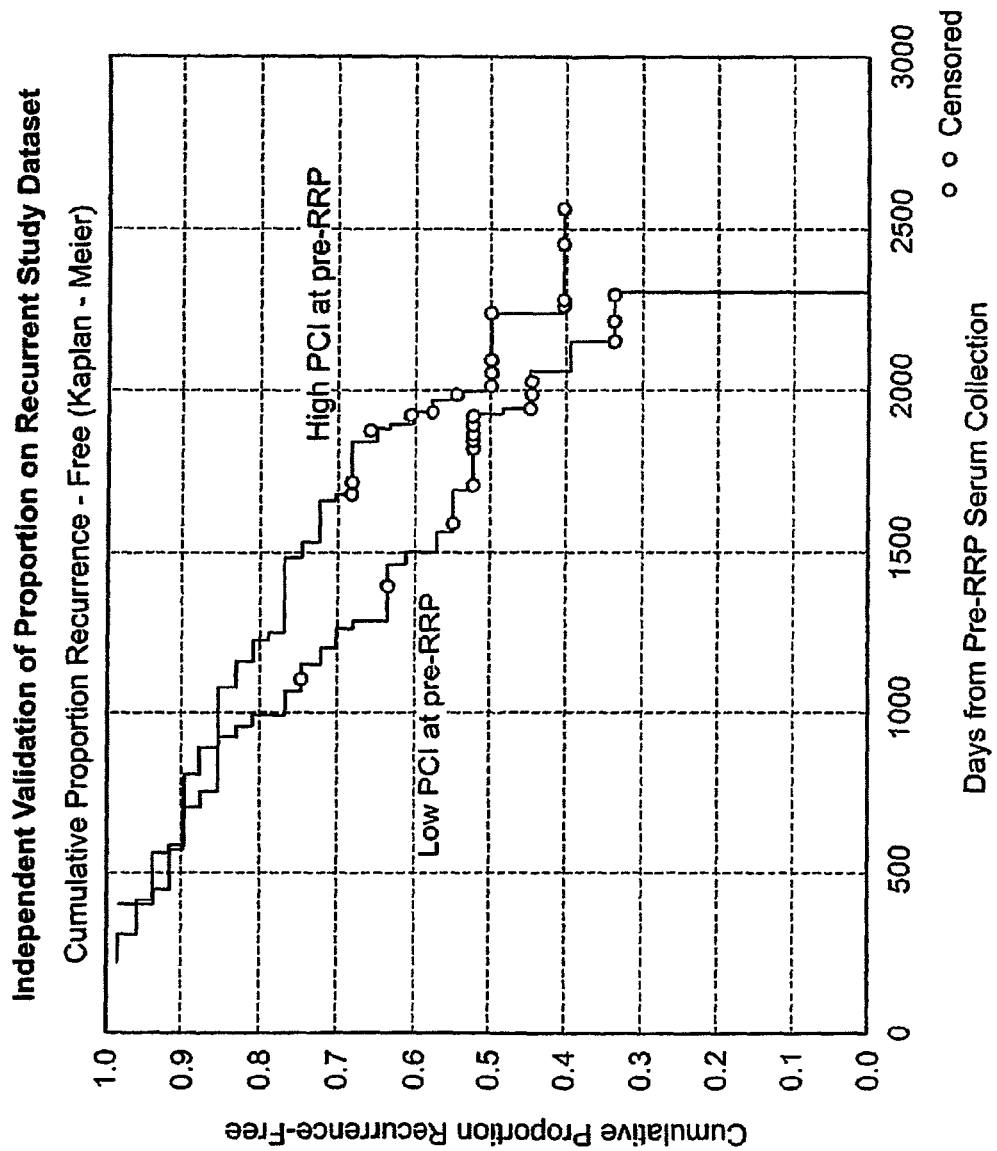
FIG. 20 is an illustration of independent validation of PCI on recurrent study dataset.
Figure 21:
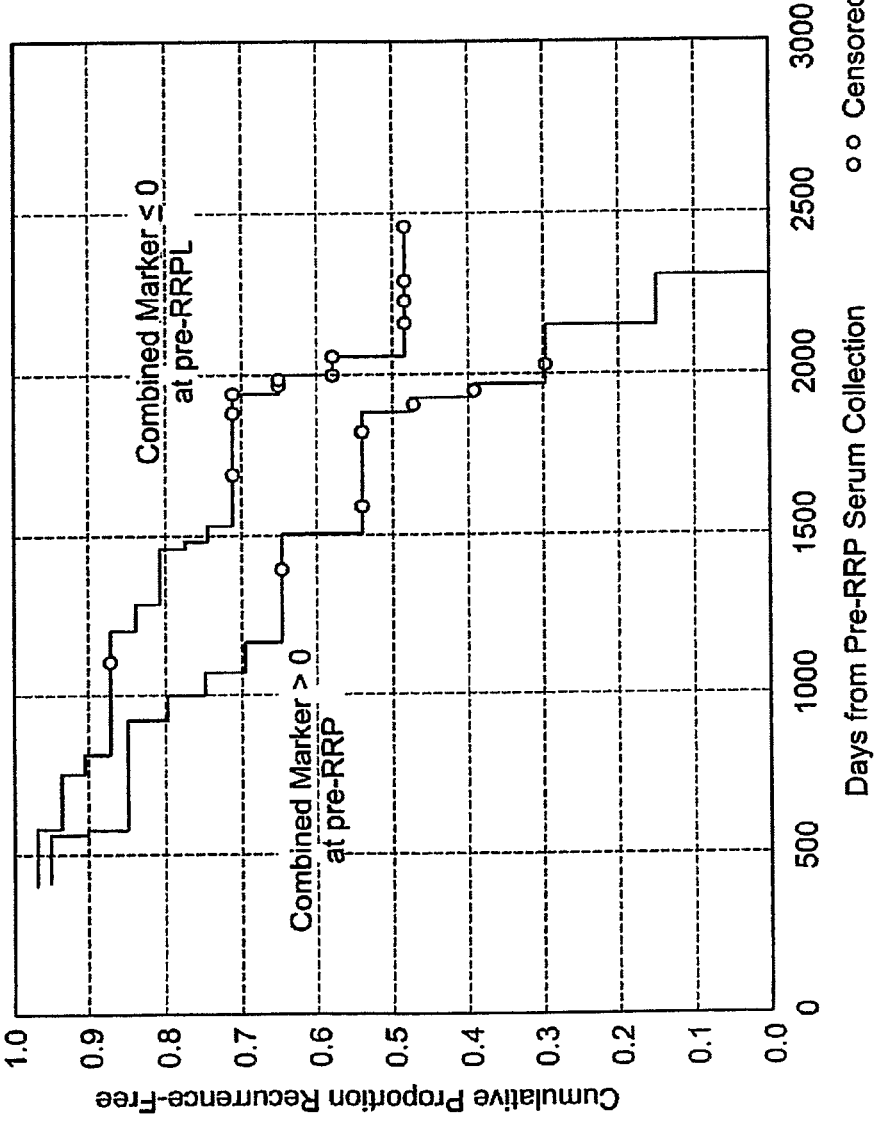
FIG. 21 is an illustration of a combination of Pre-RRP PSA, PCI and C4a using part of the Recurrent Samples as a Training Set.
Figure 22:
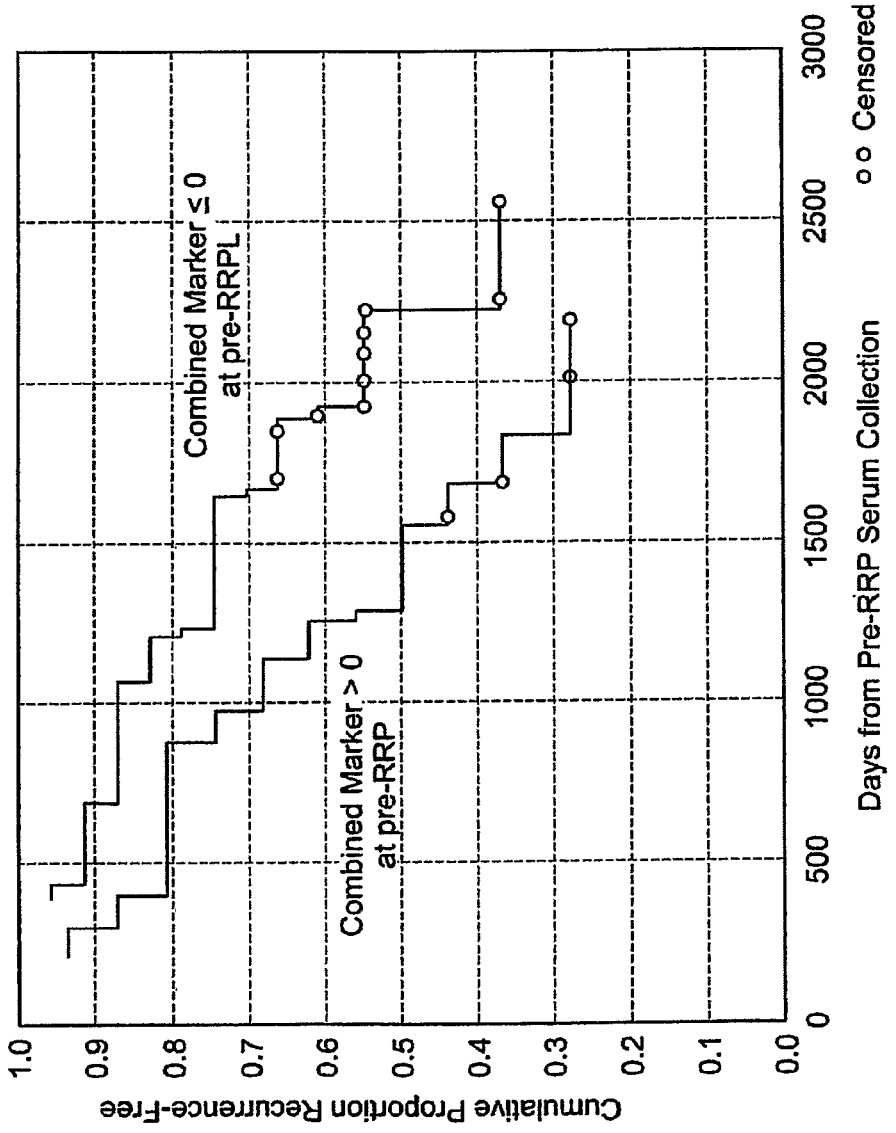
FIG. 22 is an illustration of a combination of Pre-RRP PSA, PCI and C4a using part of the Recurrent Samples as a Training Set as a Test Set.
Figure 23:
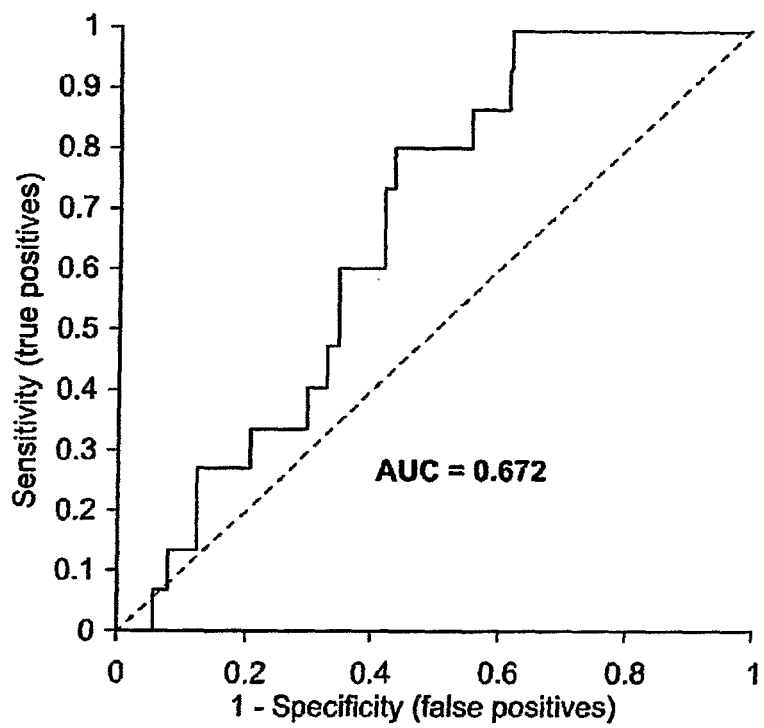
FIG. 23 is a graphic representation of ROC analysis of PCI peak separating prostate cancer patients with a Gleason Score at 5-7 from patients with a Gleason Score at 8 and above.
Figure 24:
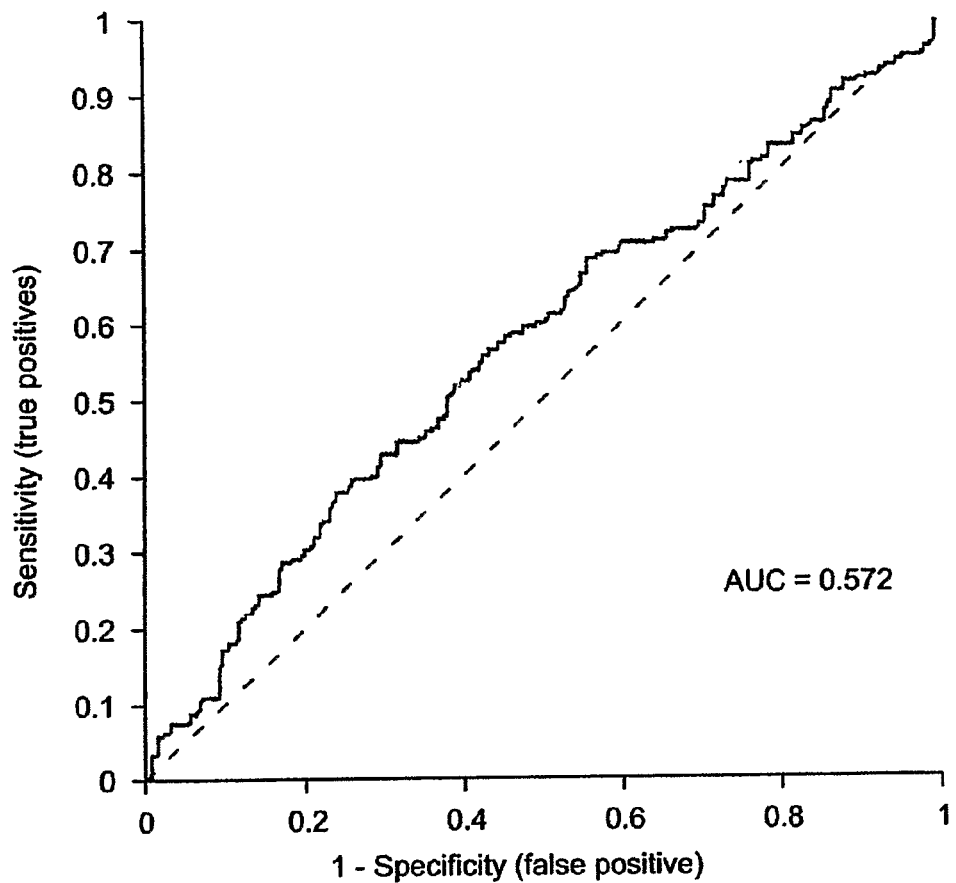
FIG. 24 is a graphic representation of ROC analysis of PCI peak in separating prostate cancer patients from patients with benign prostate disease.

The tentative candidate for the 3890 Da peptide was directly confirmed by beads-based immunoassay using whole serum and anti-Protein C inhibitor antibody (FIG. 15).

REFERENCES

1. Suzuki, K. Protein C inhibitor. Methods Enzymol, 222: 385-399, 1993.
2. Glasscock, L. N., Rehault, S. M., Gregory, C. W., Cooper, S. T., Jackson, T. P., Hoffman, M., and Church, F. C. Protein C inhibitor (plasminogen activator inhibitor-3) expression in the CWR22 prostate cancer xenograft. Exp Mol Pathol, 79: 23-32, 2005.
3. Suzuki, K., Deyashiki, Y., Nishioka, J., and Toma, K. Protein C inhibitor: structure and function. Thromb Haemost, 61: 337-342, 1989.
4. Suzuki, K., Deyashiki, Y., Nishioka, J., Kurachi, K., Akira, M., Yamamoto, S., and Hashimoto, S. Characterization of a cDNA for human protein C inhibitor. A new member of the plasma serine protease inhibitor superfamily. J Biol Chem, 262: 611-616, 1987.
5. Suzuki, K., Nishioka, J., and Hashimoto, S. Protein C inhibitor. Purification from human plasma and characterization. J Biol Chem, 258: 163-168, 1983.
6. Cao, Y., Becker, C., Lundwall, A., Christensson, A., Gadaleanu, V., Lilja, H., and Bjartell, A. Expression of protein C inhibitor (PCI) in benign and malignant prostatic tissues. Prostate, 57: 196-204, 2003.
7. Clauss, A., Lilja, H., and Lundwall, A. A locus on human chromosome 20 contains several genes expressing protease inhibitor domains with homology to whey acidic protein. Biochem J, 368: 233-242, 2002.
8. Strandberg, K., Kjellberg, M., Knebel, R., Lilja, H., and Stenflo, J. A sensitive immunochemical assay for measuring the concentration of the activated protein C-protein C inhibitor complex in plasma: use of a catcher antibody specific for the complexed/cleaved form of the inhibitor. Thromb Haemost, 86: 604-610, 2001.
9. Christensson, A. and Lilja, H. Complex formation between protein C inhibitor and prostate-specific antigen in vitro and in human semen. Eur J Biochem, 220: 45-53, 1994.
10. Laurell, M., Christensson, A., Abrahamsson, P. A., Stenflo, J., and Lilja, H. Protein C inhibitor in human body fluids. Seminal plasma is rich in inhibitor antigen deriving from cells throughout the male reproductive system. J Clin Invest, 89: 1094-1101, 1992.
11. Otlewski, J., Jelen, F., Zakrzewska, M., and Oleksy, A. The many faces of protease-protein inhibitor interaction. Embo J, 24: 1303-1310, 2005.

What is claimed is:

1. A method of determining the probability of prostate cancer recurrence in a subject having a history of prostate cancer comprising:
   (a) measuring Protein C Inhibitor (PCI) and C4a biomarkers in a blood, serum, or plasma sample from the subject by mass spectrometry or immunoassay to determine the presence, absence, or level of the measured PCI and C4a biomarkers; and
   (b) correlating the measurements of the presence, absence, or level of the measured PCI and C4a biomarkers with prostate cancer recurrence.

2. The method of claim 1, wherein the mass spectrometry is performed with a mass spectrometer selected from the group consisting of a time-of-flight mass spectrometer, a magnetic sector mass spectrometer, a quadrupole filter mass spectrometer, an ion trap mass spectrometer, an ion cyclotron resonance mass spectrometer, an electrostatic sector analyzer mass spectrometer, a laser desorption mass spectrometer, a tandem mass spectrometer, and a hybrid of any of these types of mass spectrometers.

3. The method of claim 1, wherein the mass spectrometry is performed with a laser desorption mass spectrometer.

4. The method of claim 1, wherein the immunoassay is selected from the group consisting of an enzyme-linked immunosorbent assay (ELISA), a fluorescence-based immunoassay, and a surface-enhanced laser desorption/ionization (SELDI)-based immunoassay.

5. The method of claim 1, further comprising: fractionating the blood, serum, or plasma sample from the subject; and measuring the presence, absence, or level of the measured PCI and C4a biomarkers in the blood, serum, or plasma sample fractions by surface-enhanced laser desorption/ionization mass spectrometry.

\* \* \* \* \*

```
                      SEQUENCE LISTING

<160> NUMBER OF SEQ ID NOS: 12

<210> SEQ ID NO 1
<211> LENGTH: 33
<212> TYPE: PRT
<213> ORGANISM: Homo sapiens

<400> SEQUENCE: 1

Arg Ser Ala Arg Leu Asn Ser Gln Arg Leu Val Phe Asn Arg Pro Phe
1               5                   10                  15

Leu Met Phe Ile Val Asp Asn Asn Asp Phe Leu Gly Lys Val Asn Arg
            20                  25                  30

Phe

<210> SEQ ID NO 2
<211> LENGTH: 5
<212> TYPE: PRT
<213> ORGANISM: Homo sapiens

<400> SEQUENCE: 2

Leu Phe Leu Gly Lys
1               5

<210> SEQ ID NO 3
<211> LENGTH: 11
<212> TYPE: PRT
<213> ORGANISM: Homo sapiens

<400> SEQUENCE: 3

Arg Leu Asn Ser Gln Arg Leu Val Phe Asn Arg
1               5                   10

<210> SEQ ID NO 4
<211> LENGTH: 12
<212> TYPE: PRT
<213> ORGANISM: Homo sapiens

<400> SEQUENCE: 4

Asp Asn Asn Ile Leu Phe Leu Gly Lys Val Asn Arg
1               5                   10
```

```
<210> SEQ ID NO 5
<211> LENGTH: 11
<212> TYPE: PRT
<213> ORGANISM: Homo sapiens

<400> SEQUENCE: 5

Arg Leu Asn Ser Gln Arg Leu Val Glu Asn Arg
1               5                   10

<210> SEQ ID NO 6
<211> LENGTH: 20
<212> TYPE: PRT
<213> ORGANISM: Homo sapiens

<400> SEQUENCE: 6

Ser Gln Arg Leu Val Phe Asn Arg Pro Phe Leu Met Phe Thr Val Asp
1               5                   10                  15

Asn Asn Ile Leu
            20

<210> SEQ ID NO 7
<211> LENGTH: 20
<212> TYPE: PRT
<213> ORGANISM: Homo sapiens

<400> SEQUENCE: 7

Ala Arg Leu Asn Ser Gln Arg Leu Val Phe Asn Arg Pro Phe Leu Met
1               5                   10                  15

Phe Ile Val Asp
            20

<210> SEQ ID NO 8
<211> LENGTH: 21
<212> TYPE: PRT
<213> ORGANISM: Homo sapiens

<400> SEQUENCE: 8

Arg Leu Val Phe Asn Arg Pro Phe Leu Met Phe Ile Ile Val Asp Asn
1               5                   10                  15

Asn Ile Leu Phe Leu
            20

<210> SEQ ID NO 9
<211> LENGTH: 33
<212> TYPE: PRT
<213> ORGANISM: Homo sapiens

<400> SEQUENCE: 9

Ser Ala Arg Leu Asn Ser Gln Arg Leu Val Phe Asn Arg Pro Phe Leu
1               5                   10                  15

Met Phe Ile Val Asp Asn Asn Ile Leu Phe Leu Gly Lys Val Asn Arg
            20                  25                  30

Pro

<210> SEQ ID NO 10
<211> LENGTH: 406
<212> TYPE: PRT
<213> ORGANISM: Homo sapiens

<400> SEQUENCE: 10

Met Gln Leu Phe Leu Leu Leu Cys Leu Val Leu Leu Ser Pro Gln Gly
1               5                   10                  15

Ala Ser Leu His Arg His His Pro Arg Glu Met Lys Lys Arg Val Glu
```

```
                    20                  25                  30
Asp Leu His Val Gly Ala Thr Val Ala Pro Ser Ser Arg Arg Asp Phe
                35                  40                  45

Thr Phe Asp Leu Tyr Arg Ala Lys Ala Ser Ala Ala Pro Ser Gln Asn
            50                  55                  60

Ile Phe Phe Ser Pro Val Ser Ile Ser Met Ser Leu Ala Met Leu Ser
65                  70                  75                  80

Leu Gly Ala Gly Ser Ser Thr Lys Met Gln Ile Leu Glu Gly Leu Gly
                85                  90                  95

Leu Asn Leu Gln Lys Ser Ser Glu Lys Glu Leu His Arg Gly Phe Gln
            100                 105                 110

Gln Leu Leu Gln Glu Leu Asn Gln Pro Arg Asp Gly Phe Gln Leu Ser
        115                 120                 125

Leu Gly Asn Ala Leu Phe Thr Asp Leu Val Val Asp Leu Gln Asp Thr
    130                 135                 140

Phe Val Ser Ala Met Lys Thr Leu Tyr Leu Ala Ser Thr Phe Pro Thr
145                 150                 155                 160

Asn Phe Arg Asp Ser Ala Gly Ala Met Lys Gln Ile Asn Asp Tyr Val
                165                 170                 175

Ala Lys Gln Thr Lys Gly Lys Ile Val Asp Leu Leu Lys Asn Leu Asp
            180                 185                 190

Ser Asn Ala Val Val Thr Met Val Asn Tyr Ile Phe Phe Lys Ala Lys
        195                 200                 205

Trp Phe Thr Ser Phe Asn His Lys Gly Thr Gln Glu Gln Asp Phe Tyr
    210                 215                 220

Val Thr Ser Glu Thr Val Val Arg Val Pro Met Met Ser Arg Glu Asp
225                 230                 235                 240

Gln Tyr His Tyr Leu Leu Asp Arg Asn Leu Ser Cys Arg Val Val Gly
                245                 250                 255

Val Pro Tyr Gln Gly Asn Ala Thr Ala Leu Phe Ile Leu Pro Ser Glu
            260                 265                 270

Gly Lys Met Gln Gln Val Glu Asn Gly Leu Ser Glu Lys Thr Leu Arg
        275                 280                 285

Lys Trp Leu Lys Met Phe Lys Lys Arg Gln Leu Glu Leu Tyr Leu Pro
    290                 295                 300

Lys Phe Ser Ile Glu Gly Ser Tyr Gln Leu Glu Lys Val Leu Pro Ser
305                 310                 315                 320

Leu Gly Ile Ser Asn Val Phe Thr Ser His Ala Asp Leu Ser Gly Ile
                325                 330                 335

Ser Asn His Ser Asn Ile Gln Val Ser Glu Met Val His Lys Ala Val
            340                 345                 350

Val Glu Val Asp Glu Ser Gly Thr Arg Ala Ala Ala Thr Gly Thr
        355                 360                 365

Ile Phe Thr Phe Arg Ser Ala Arg Leu Asn Ser Gln Arg Leu Val Phe
    370                 375                 380

Asn Arg Pro Phe Leu Met Phe Ile Val Asp Asn Asn Ile Leu Phe Leu
385                 390                 395                 400

Gly Lys Val Asn Arg Pro
                405

<210> SEQ ID NO 11
<211> LENGTH: 10
<212> TYPE: PRT
<213> ORGANISM: Artificial Sequence
<220> FEATURE:
```

-continued

```
<223> OTHER INFORMATION: Description of Artificial Sequence: Synthetic
      peptide

<400> SEQUENCE: 11

Glu Glu Glu Glu Glu Glu Glu Glu Glu Glu
1               5                   10

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Asp Asp Asp Asp Asp Asp Asp Asp
1               5
```